United States Patent
Shiflett et al.

(10) Patent No.: US 12,404,224 B2
(45) Date of Patent: Sep. 2, 2025

(54) PROCESS FOR SEPARATING COMPONENTS OF AZEOTROPIC MIXTURES USING IONIC LIQUIDS

(71) Applicant: University of Kansas, Lawrence, KS (US)

(72) Inventors: Mark Brandon Shiflett, Lawrence, KS (US); Ana Rita Colaco Morais, Lakewood, CO (US)

(73) Assignee: University of Kansas, Lawrence, KS (US)

( * ) Notice: Subject to any disclaimer, the term of this patent is extended or adjusted under 35 U.S.C. 154(b) by 196 days.

(21) Appl. No.: 17/768,287

(22) PCT Filed: Oct. 13, 2020

(86) PCT No.: PCT/US2020/055338
§ 371 (c)(1),
(2) Date: Apr. 12, 2022

(87) PCT Pub. No.: WO2021/076480
PCT Pub. Date: Apr. 22, 2021

(65) Prior Publication Data
US 2024/0182386 A1  Jun. 6, 2024

Related U.S. Application Data

(60) Provisional application No. 63/060,230, filed on Aug. 3, 2020, provisional application No. 62/915,074, filed on Oct. 15, 2019.

(51) Int. Cl.
*C07C 17/386* (2006.01)

(52) U.S. Cl.
CPC .................. *C07C 17/386* (2013.01)

(58) Field of Classification Search
CPC ........................... C07C 17/383–386
See application file for complete search history.

(56) References Cited

U.S. PATENT DOCUMENTS

| | | |
|---|---|---|
| 5,087,329 A | 2/1992 | Felix |
| 5,211,817 A | 5/1993 | Adams et al. |
| 5,523,499 A | 6/1996 | Corbin et al. |
| 6,156,161 A | 12/2000 | Miller |
| 7,273,835 B2 | 9/2007 | Pham et al. |
| 7,964,760 B2 | 6/2011 | Shiflett et al. |
| 8,628,644 B2 | 1/2014 | Shiflett et al. |
| 2007/0131535 A1* | 6/2007 | Shiflett .................. C07B 63/00 203/99 |
| 2008/0293978 A1* | 11/2008 | Shiflett ................ C07C 17/386 570/177 |
| 2018/0155594 A1 | 6/2018 | France |

OTHER PUBLICATIONS

The International Search Report and the Written Opinion issued on Jan. 29, 2021 for international patent application No. PCT/US2020/055338; pp. 1-8.
Shiflett, M. B.; Harmer, M. A.; Junk, C. R.; Yokozeki, A., Solubility and diffusivity of 1,1,1,2-tetrafluoroethane in room-temperature ionic liquids. Fluid Phase Equilibr 2006, 242, (2), 220-232.
Shiflett, M. B.; Yokozeki, A., Solubility and diffusivity of hydrofluorocarbons in room-temperature ionic liquids. AlChE journal 2006, 52, (3), 1205-1219.
Ren, W.; Scurto, A. M., Phase equilibria of imidazolium ionic liquids and the refrigerant gas, 1,1,1,2-tetrafluoroethane (R-134a). Fluid Phase Equilibr 2009, 286, (1), 1-7.
Sosa, J. E.; Ribeiro, R. P.; Castro, P. J.; Mota, J. P.; Araújo, J. M.; Pereiro, A. B., Absorption of Fluorinated Greenhouse Gases Using Fluorinated Ionic Liquids. Ind Eng Chem Res 2019, 58, (45), 20769-20778.
Mark B. Shiflett et al., "Separation of difluoromethane and pentafluoroethane by extractive distillation using ionic liquid," Chemistry Today, vol. 24, No. 2, Mar./Apr. 2006; pp. 28-30.
Sosa, J. E.; Ribeiro, R. P.; Castro, P. J.; Mota, J. P.; Araújo, J. M.; Pereiro, A. B., Supporting Information—Absorption of Fluorinated Greenhouse Gases Using Fluorinated Ionic Liquids. Ind Eng Chem Res 2019, 58, (45), 20769-20778.

* cited by examiner

*Primary Examiner* — Medhanit W Bahta
(74) *Attorney, Agent, or Firm* — Bell & Manning, LLC

(57) ABSTRACT

Processes for separating an azeotropic mixture are provided. In an embodiment, such a process comprises exposing an azeotropic mixture comprising a first (hydro)fluorocarbon and a second (hydro)fluorocarbon to an ionic liquid comprising a cation and a non-fluorinated anion at a temperature and a pressure at which the ionic liquid absorbs more of one of the first and second (hydro)fluorocarbons than another of the first and second (hydro)fluorocarbons as determined on a mass basis to form a (hydro)fluorocarbon-containing ionic liquid and a processed azeotropic mixture.

1 Claim, 17 Drawing Sheets

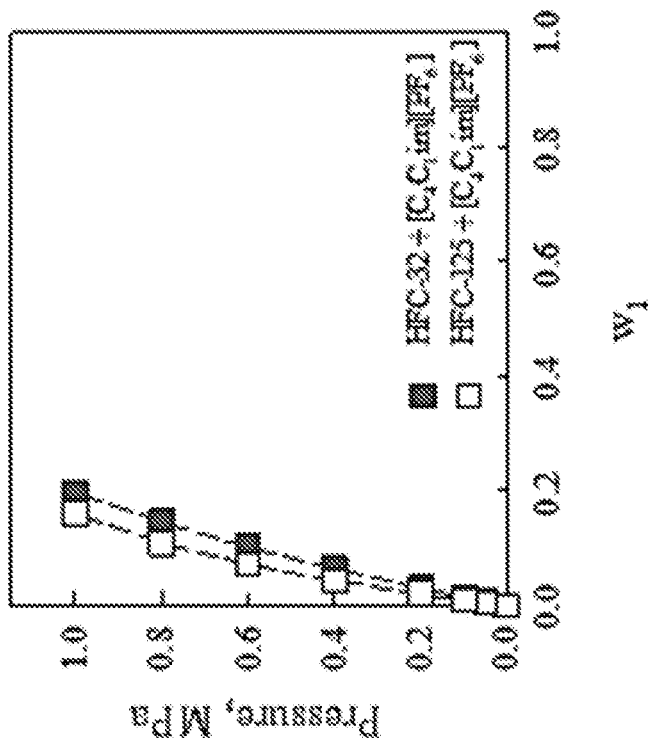
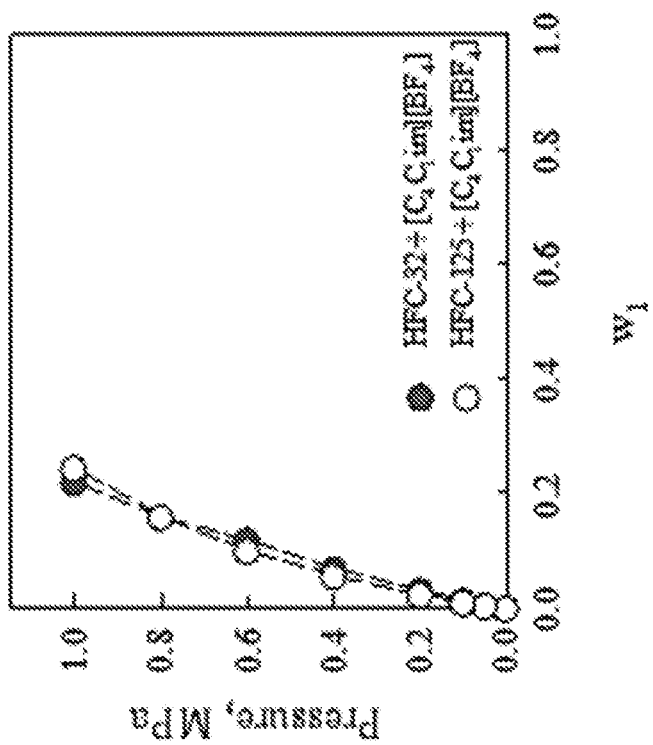
FIG. 11A
FIG. 11B

PROCESS FOR SEPARATING COMPONENTS OF AZEOTROPIC MIXTURES USING IONIC LIQUIDS

CROSS-REFERENCE TO RELATED APPLICATIONS

This application is a National Stage of International Application No. PCT/US20/55338, filed Oct. 13, 2020, which claims priority to U.S. provisional patent application No. 62/915,074 that was filed Oct. 15, 2019 and U.S. provisional patent application No. 63/060,230 that was filed on Aug. 3, 2020, the entire contents of each of which are incorporated herein by reference.

BACKGROUND

Refrigerant mixtures are typically composed of two (binary) or three (ternary) pure refrigerants. Many of these mixtures are azeotropic or near-azeotropic and behave like a pure fluid, that is under constant pressure they condense and evaporate at a constant temperature and the composition of the mixture in the vapor and liquid phases will be essentially the same. Thus, any refrigerant leak from an azeotropic mixture does not change the composition of the remaining refrigerant. While this is essential for modern cooling systems, it greatly complicates refrigerant recycling and responsible disposal.

SUMMARY

The present disclosure describes the separation of (hydro) fluorocarbons in azeotropic mixtures that cannot be separated using differences in boiling points by distillation. Ionic liquids have been identified that can absorb large quantities of (hydro)fluorocarbon refrigerants as well as differentiate between different types of (hydro)fluorocarbons.

In an embodiment, a process for separating an azeotropic mixture comprises exposing an azeotropic mixture comprising a first (hydro)fluorocarbon and a second (hydro)fluorocarbon to an ionic liquid comprising a cation and a non-fluorinated anion at a temperature and a pressure at which the ionic liquid absorbs more of one of the first and second (hydro)fluorocarbons than another of the first and second (hydro)fluorocarbons as determined on a mass basis to form a (hydro)fluorocarbon-containing ionic liquid and a processed azeotropic mixture.

In another embodiment, a process for separating an azeotropic mixture comprises exposing an azeotropic mixture comprising difluoromethane and pentafluoroethane to an ionic liquid comprising a cation and a non-fluorinated anion at a temperature and a pressure at which the ionic liquid absorbs more of one of difluoromethane and pentafluoroethane than another of difluoromethane and pentafluoroethane as determined on a mass basis to form a (hydro) fluorocarbon-containing ionic liquid and a processed azeotropic mixture.

In another embodiment, a process for separating an azeotropic mixture comprises exposing an azeotropic mixture comprising pentafluoroethane and 1,1,1-trifluoroethane to an ionic liquid comprising a cation and a non-fluorinated anion at a temperature and a pressure at which the ionic liquid absorbs more of one of pentafluoroethane and 1,1,1-trifluoroethane than another of pentafluoroethane and 1,1,1-trifluoroethane as determined on a mass basis to form a (hydro)fluorocarbon-containing ionic liquid and a processed azeotropic mixture.

Other principal features and advantages of the disclosure will become apparent to those skilled in the art upon review of the following drawings, the detailed description, and the appended claims.

BRIEF DESCRIPTION OF THE DRAWINGS

Illustrative embodiments of the disclosure will hereafter be described with reference to the accompanying drawings.

(FIG. 10A) $[C_4C_1im][BF_4]$, (FIG. 10B) $[C_4C_1im][PF_6]$, (FIG. 10C) $[C_6C_1im][FAP]$, (FIG. 10D) $[C_4C_1im][C_1CO_2]$, (FIG. 10E) $[C_4C_1im][SCN]$, and (FIG. 10F) $[C_6C_1im][Cl]$ at 298.15 K.

FIGS. 11A-11F show comparison of HFC-32 and HFC-125 VLE (mass fraction, $w_1$) in ionic liquids: (FIG. 11A) $[C_4C_1im][BF_4]$, (FIG. 11B) $[C_4C_1im][PF_6]$, (FIG. 11C) $[C_6C_1im][FAP]$, (FIG. 11D) $[C_4C_1im][C_1CO_2]$, (FIG. 11E) $[C_4C_1im][SCN]$, and (FIG. 11F) $[C_6C_1im][Cl]$ at 298.15 K.

DETAILED DESCRIPTION

Figure 1A:
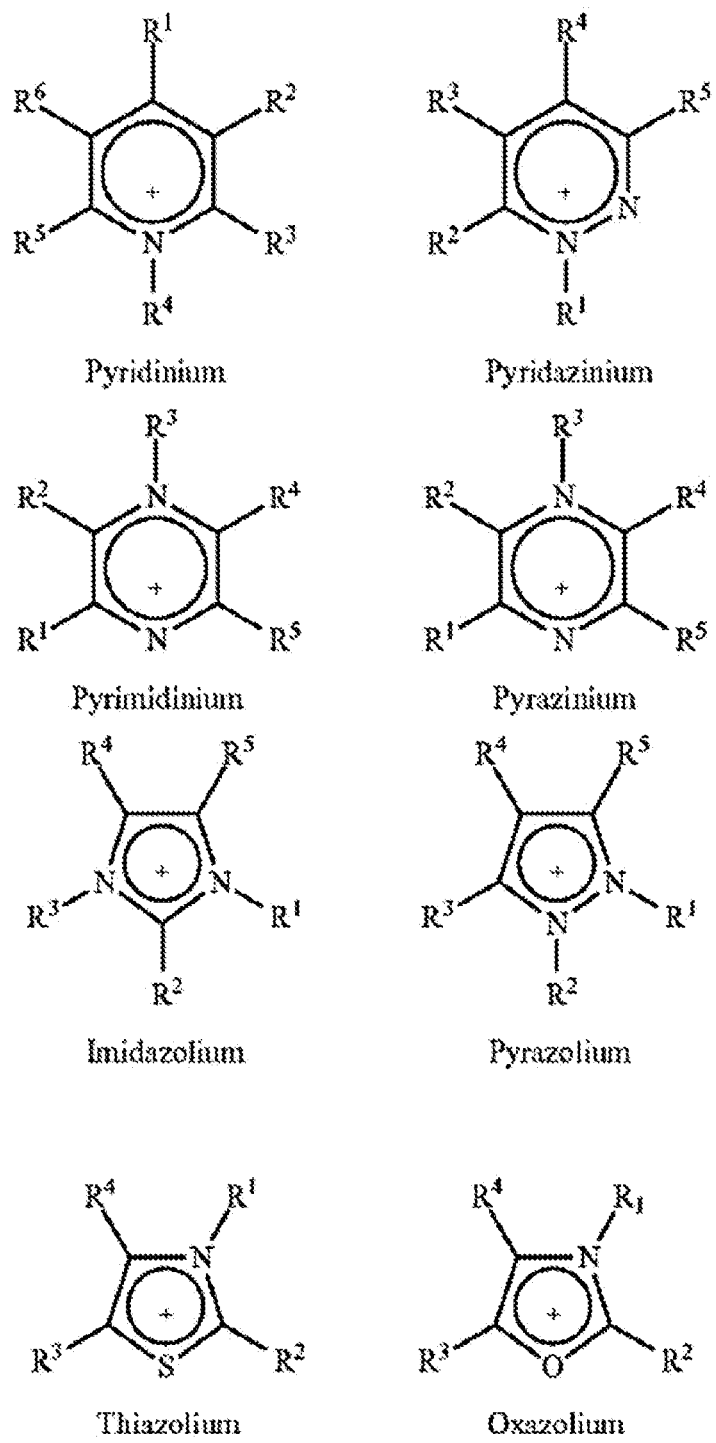
FIGS. 1A-1C show illustrative cations which may be used to form an ionic liquid for use in the present processes.

Common refrigerants, their composition, environmental impact, and regulatory status are summarized in Table 1. Chlorofluorocarbons (CFCs) and hydrochlorofluorocarbons (HCFCs) refrigerants, such as R-502 and R-22 ($CHF_2Cl$), respectively, were phased out under the Montreal Protocol in 1987 because of their high ozone depletion potential (ODP). This drove development of more environmentally friendly refrigerants and refrigerant mixtures. For example, R-404a, a near-azeotropic mixture composed of HFCs R-125 ($CHF_2CF_3$), R-143a ($CH_3CF_3$), and R-134a ($CH_2FCF_3$), and R-507, an azeotropic mixture composed of R-125 and R-143a are common replacements for R-502. R-22, which is widely used in residential and commercial air-conditioning equipment, was replaced with the binary azeotropic mixture R-410a (R-32 and R-125) and the near-azeotropic mixture R-407c (R-32, R-125, R-134a). Unfortunately, many HFCs, including R-404a, R-507, R-410a, and R-407c, exhibit high global warming potentials (GWP). For example, R-125, a component in these four azeotropic mixtures, has a GWP 3500 times higher than that of $CO_2$. Recent international efforts including the Kigali Amendment in 2016 and the European Union F-Gas regulations in 2015 seek to reduce the use of high GWP refrigerants through restrictions for use in new equipment and ongoing phaseouts planned through the 2020s. Thus, it would be extremely useful to recover R-32 ($CH_2F_2$), which has a much lower GWP than the other HFCs, from the millions of kilograms of R-410a and R-407c currently on the market so that it can be reused. However, it is not currently possible to easily separate R-32 from R-125, which form an azeotropic mixture. Furthermore, separating R-125 from R-143a is also currently not possible, and separating R-125 from R-134a is energy intensive.

Without the ability to separate R-32 from these other refrigerants, the phase-out of R-410a and R-407c will require that the refrigerants be reclaimed and incinerated or simply vented to the atmosphere. Incineration is wasteful and likely to lead to the release of hazardous emissions, while venting will release huge quantities of long-lived potent greenhouse gases to the atmosphere. Furthermore, preventing the release of the R-125 back into the atmosphere would be equivalent to eliminating 175 million metric tons of $CO_2$ (or emissions from 35 million cars in one year).

The present disclosure provides a process for separating (extracting) components of azeotropic mixtures. The phrase "azeotropic mixture" and the like encompasses near-azeotropic mixtures and refers to a mixture of two or more components (e.g., 2, 3, etc.) in which the composition of the vapor phase and the liquid phase are the same or nearly the same at a selected pressure and temperature. The phrase also refers to mixtures of components in which the components have normal boiling point temperatures that are the same or within 10° C. of each other or less (including, within 9° C., 8° C., 7° C., 6° C., 5° C., 4° C., 3° C., 2° C., or 1° C.).

The components of the azeotropic mixtures may be fluorocarbons, hydrofluorocarbons, or combinations thereof. The term "(hydro)fluorocarbon" refers to both fluorocarbons and hydrofluorocarbons. A "fluorocarbon" is a compound comprising fluorine and carbon, but not hydrogen. A fluorocarbon compound includes an FC-fluorocarbon compound ("FC"), which consists solely of fluorine and carbon, as well as a chlorofluorocarbon (CFC) compound, wherein FC and CFC are known terms used to define refrigerants. Fluorocarbon compounds also include, however, compounds selected from the group consisting of fluoroether compounds, fluoroketone compounds, fluoroaromatic compounds and fluoroolefin compounds. Fluorocarbon compounds also include compounds wherein one or more optional substituents therein may be selected from one or more of bromine, chlorine and iodine. A "hydrofluorocarbon" is a compound comprising fluorine, carbon and at least one hydrogen atom. A hydrofluorocarbon compound includes an HFC-hydrofluorocarbon compound ("HFC"), which consists solely of fluorine, carbon and hydrogen, as well as a hydrochlorofluorocarbon (HCFC) compound, wherein HFC and HCFC are known terms used to define refrigerants. Hydrofluorocarbon compounds also include, however, compounds selected from the group consisting of hydrofluoroether compounds, hydrofluoroketone com-

TABLE 1

Summary of refrigerants, their composition, environmental impact, and regulatory status. ODP: ozone depletion potential with baseline R-11 = 1. GWP: 100-year greenhouse warming potential with baseline $CO_2$ = 1. Montreal Protocol (M): x phase down, xx global ban. Kigali agreement (K): ✓ low-GWP, x high-GWP. EU F-Gas (F): ✓ no controls, x some restrictions, xx substantial restrictions

| Type | Name | Composition (wt. % for mixtures) | ODP | GWP | M | K | F |
| --- | --- | --- | --- | --- | --- | --- | --- |
| CFC | R-115 | chloropentafluoroethane | 0.6 | 7370 | xx | x | xx |
|  | R-502 | 48.8% R-22, 51.2% R-115 | 0.33 | 4657 | xx | x | xx |
| HCFC | R-22 | chlorodifluoromethane | 0.055 | 1810 | x | x | x |
| HFC | R-143a | 1,1,1-trifluoroethane | 0 | 4470 |  | x | xx |
|  | R-404a | 44% R-125, 52% R-143a, 4% R-134a | 0 | 3922 |  | x | xx |
|  | R-507 | 50% R-125, 50% R-143a | 0 | 3900 |  | x | xx |
|  | R-125 | pentafluoroethane | 0 | 3500 |  | x | xx |
|  | R-410a | 50% R-32, 50% R-125 | 0 | 2088 |  | x | x |
|  | R-407c | 23% R-32, 25% R-125, 52% R-134a | 0 | 1774 |  | x | x |
|  | R-134a | 1,1,1,2-tetrafluoroethane | 0 | 1430 |  | x | x |
|  | R-32 | difluoromethane | 0 | 675 |  | ✓ | x |
|  | R-152a | 1,1-difluoroethane | 0 | 124 |  | ✓ | ✓ |
| HFO | R-1234yf | 2,3,3,3-tetrafluoropropene | 0 | 4 |  | ✓ | ✓ |
|  | R-1234ze | 1,3,3,3-tetrafluoropropene | 0 | 7 |  | ✓ | ✓ |
| HCFO | R-1233zd(E) | trans-1-chloro-3,3,3-trifluoro-1-propene | <0.01 | 4 |  | ✓ | ✓ |
|  | R-1233zd(Z) | cis-1-chloro-3,3,3-trifluoro-1-propene | <0.01 | 4 |  | ✓ | ✓ |
| HFO/HFC | R-513a | 56% R-1234yf, 44% R-134a | 0 | 631 |  | ✓ | ✓ | pounds, hydrofluoroaromatic compounds and hydrofluoroolefin compounds. Hydrofluorocarbon compounds also include compounds wherein one or more optional substituents therein may be selected from one or more of bromine, chlorine and iodine.

Illustrative azeotropic mixtures are provided in Table 1. In embodiments, the azeotropic mixture comprises pentafluoroethane (R-125). In embodiments, the azeotropic mixture comprises difluoromethane (R-32). In embodiments, the azeotropic mixture comprises pentafluoroethane (R-125) and difluoromethane (R-32). In embodiments, the azeotropic mixture comprises pentafluoroethane (R-125) and 1,1,1-trifluoroethane (R-143a). In embodiments, the azeotropic mixture comprises pentafluoroethane (R-125), 1,1,1-trifluoroethane (R-143a), and 1,1,1,2-tetrafluoroethane (R-134a). In embodiments, the azeotropic mixture is R-410a (50 mass % R-32 and 50 mass % R-125). In embodiments, the azeotropic mixture is R-507 (50 mass % R-125 and 50 mass % R-143a). In embodiments, the azeotropic mixture is R-404a (44 mass % R-125, 52 mass % R-143a, and 4 mass % R-134a).

In the present process, the azeotropic mixture is exposed to (contacted with) an ionic liquid at a temperature and a pressure at which the ionic liquid absorbs (solubilizes) a greater amount of one of the (hydro)fluorocarbons in the azeotropic mixture than another one (or the remaining) (hydro)fluorocarbons in the azeotropic mixture. Although existing processes have been developed for separating (hydro)fluorocarbons using certain ionic liquids, the present processes are based, at least in part, on new insights as described immediately below.

First, the inventors have determined that in selecting an ionic liquid for the separation, a mass basis selectivity ratio is desirably used, rather than a mole fraction selectivity ratio. The mass basis selectivity ratio ($SW_{ij}$) for (hydro)fluorocarbon i and (hydro)fluorocarbon j at a selected temperature (T) and pressure (P) is given by:

$$S_{Wij} = \left(\frac{w_{vi}/w_{li}}{w_{vj}/w_{lj}}\right)_{T,P}$$

where $w_{vi,j}$ and $w_{li,j}$ are the vapor and liquid mass fractions of the dissolved (hydro)fluorocarbon components i and j in the ionic liquid at the selected temperature and pressure where $w_{vi}$ and $w_{vj}$=1.0. (Also see Equation 23 in Example 3, below.) As described in Example 3, below, a mole fraction selectivity ratio (in which mole fractions of the dissolved (hydro)fluorocarbon component in the ionic liquid are used in place of the mass fractions) does not necessarily lead to the ionic liquid providing the most selective separation system.

Second, the inventors have determined that ionic liquids comprising non-fluorinated anions can actually achieve a more selective separation than ionic liquids comprising fluorinated anions. This is an unexpected discovery since existing wisdom has been that fluorinated anions are favored for separating (hydro)fluorocarbon azeotropic mixtures as they form the strongest hydrogen bonds. Moreover, they form hydrogen bonds with numerous (hydro)fluorocarbons to varying degrees, thereby allowing for the selective absorption of the (hydro)fluorocarbons and their efficient separations. As a result, existing approaches for separating azeotropic mixtures have been based on selecting ionic liquids having fluorinated anions. The inventors' unexpected discovery of the superiority of ionic liquids comprising non-fluorinated anions is demonstrated in Example 3, below, using an azeotropic mixture composed of pentafluoroethane (R-125) and difluoromethane (R-32) as an illustrative example.

Briefly, it was found that the mass basis selectivity ratio ($SW_{ij}$) for pentafluoroethane (R-125) and difluoromethane (R-32) in the ionic liquid 1-hexyl-3-methylimidazolium acetate ([$C_4C_1$im][Cl]) was surprisingly high as compared to the ionic liquid 1-butyl-3-methylimidzaolium hexafluorophosphate ([$C_4C_1$im][$PF_6$]) at room temperature (298.15 K) and a pressure of 1.0 MPa. Ionic liquids having fluorinated anions such as [$PF_6$] are known to strongly absorb difluoromethane (R-32) via hydrogen bonding and thus have been suggested for separating azeotropic mixtures comprising R-32. However, the inventors found that in [$C_6C_1$im][Cl], it is pentafluoroethane (not difluoromethane) that is the more strongly absorbed component, which was an unexpected result. Moreover, the $SW_{ij}$ for pentafluoroethane (R-125) and difluoromethane (R-32) at room temperature and pressure was found to be over three times greater as compared to the $SW_{ij}$ in ([$C_4C_1$im][$PF_6$]). Both the reverse in solubility behavior for R-125 and the high mass basis selectivity value demonstrate the unexpected nature of the inventors' results. Similar results were found for the use of 1-butyl-3-methylimidazolium acetate ([$C_4C_1$im][Ac]) as compared to ([$C_4C_1$im][$PF_6$]).

Finally, it is also noted that the mole fraction selectivity ratio for pentafluoroethane (R-125) and difluoromethane (R-32) in [$C_6C_1$im][Cl]) at room temperature and 1.0 MPa is actually less than the mole fraction selectivity ratio in [$C_4C_1$im][$PF_6$]. Thus, absent the inventors' insight as to the importance of considering mass basis selectivity ratios, the ionic liquid [$C_6C_1$im][Cl] would not have been selected for separating pentafluoroethane (R-125) and difluoromethane (R-32).

Aside from these considerations, a variety of ionic liquids may be used. The ionic liquids are generally organic salts that are liquids with melting points below 100° C. The ionic liquids comprise a cation and an anion. A variety of cations and non-fluorinated anions may be used. The ionic liquid may include more than one type of cation, more than one type of anion, or both. However, the ionic liquid may include a single type of cation and a single type of anion.

Figure 1B:
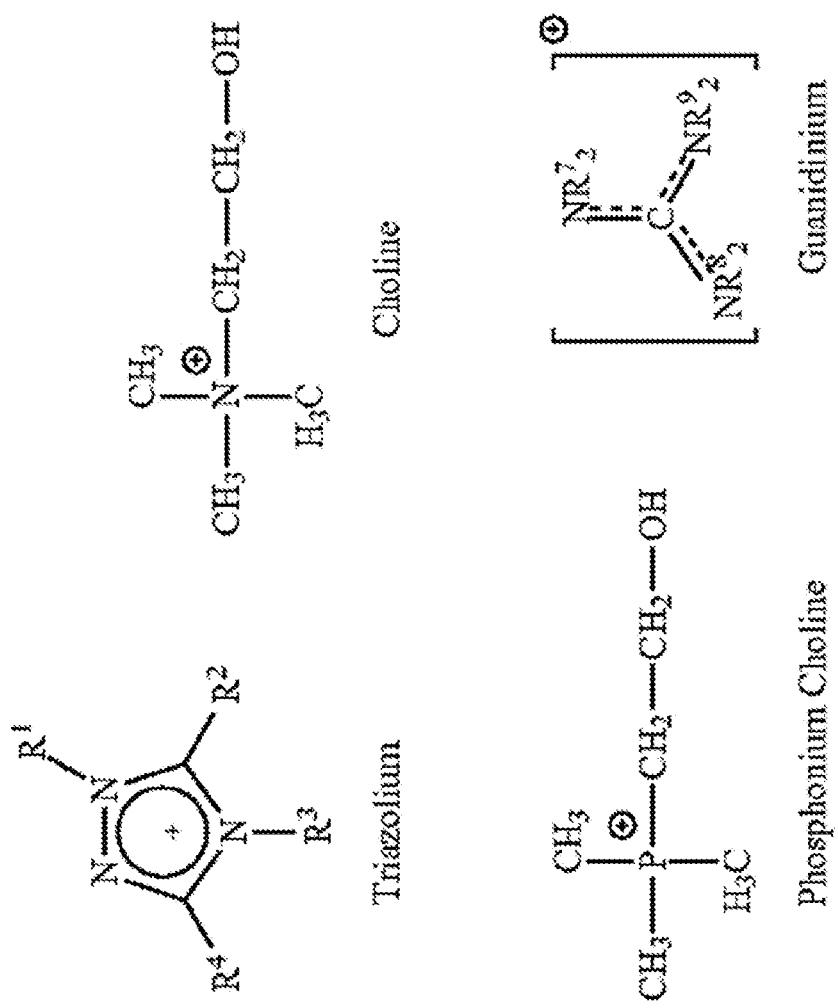
Figure 1C:
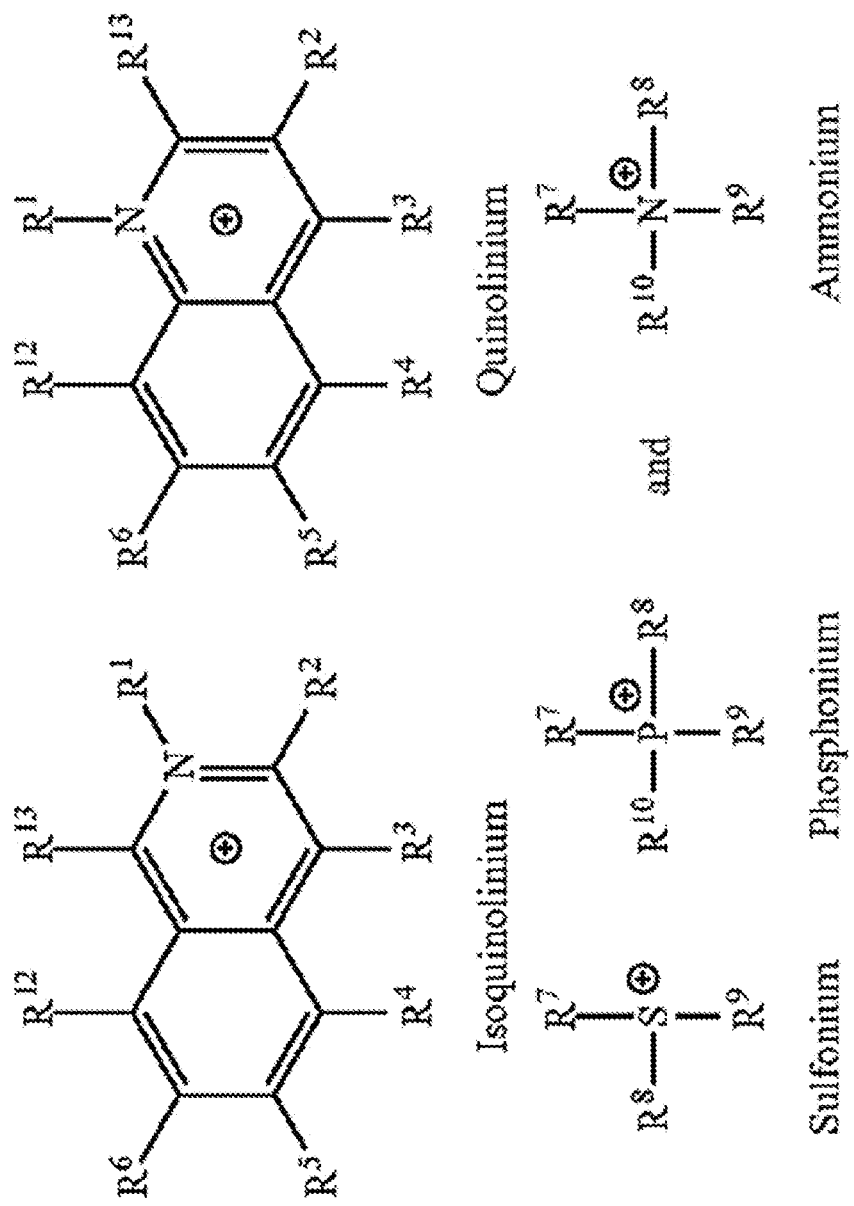

In embodiments, the cation is selected from the group consisting of cations represented by the structures of the formulae shown in FIGS. 1A-1C. In these formulae, the following provisos apply:
(a) $R^1$, $R^2$, $R^3$, $R^4$, $R^5$, $R^6$, $R^{12}$ and $R^{13}$ are independently selected from the group consisting of:
  (i) H;
  (ii) halogen such as F, Cl, Br, I;
  (iii) —$CH_3$, —$C_2H_5$, or $C_3$ to $C_{25}$ straight-chain, branched or cyclic alkane or alkene groups, optionally substituted with at least one member selected from the group consisting of Cl, Br, F, I, OH, $NH_2$ SH, and $SO_3H$;
  (iv) —$CH_3$, —$C_2H_5$, or $C_3$ to $C_{25}$ straight-chain, branched or cyclic alkane or alkene groups comprising one to three heteroatoms selected from the group consisting of O, N, Si and S, and optionally substituted with at least one member selected from the group consisting of Cl, Br, F, I, OH, $NH_2$ and SH;
  (v) $C_6$ to $C_{25}$ unsubstituted aryl, or $C_6$ to $C_{25}$ unsubstituted heteroaryl, groups having one to three heteroatoms independently selected from the group consisting of O, N, Si and S, wherein the unsubstituted aryl or unsubstituted heteroaryl may be bonded to the structure via an alkyl (e.g., —CH$_2$—) spacer group;
  (vi) C$_6$ to C$_{25}$ substituted aryl, or C$_6$ to C$_{25}$ substituted heteroaryl, groups having one to three heteroatoms independently selected from the group consisting of O, N, Si and S; wherein the substituted aryl or substituted heteroaryl may be bonded to the structure via an alkyl (e.g., —CH$_2$—) spacer group; and wherein said substituted aryl or substituted heteroaryl has one to three substituents independently selected from the group consisting of:
    (A) —CH$_3$, —C$_2$H$_5$, or C$_3$ to C$_{25}$ straight-chain, branched or cyclic alkane or alkene groups, optionally substituted with at least one member selected from the group consisting of Cl, Br, F, I, OH, NH$_2$ and SH,
    (B) OH,
    (C) NH$_2$, and
    (D) SH; and
  (vii) —(CH$_2$)$_n$Si(CH$_2$)$_m$CH$_3$, (CH$_2$)$_n$Si(CH$_3$)$_3$, (CH$_2$)$_n$OSi(CH$_3$)$_m$, where n is independently 1-4 and m is independently 0-4;
(b) R$^7$, R$^1$, R$^9$, and R$^{10}$ are independently selected from the group consisting of:
  (i) —CH$_3$, —C$_2$H$_5$, or C$_3$ to C$_{25}$ straight-chain, branched or cyclic alkane or alkene groups, optionally substituted with at least one member selected from the group consisting of Cl, Br, F, I, OH, NH$_2$, SH and SO$_3$H;
  (ii) —CH$_3$, —C$_2$H$_5$, or C$_3$ to C$_{25}$ straight-chain, branched or cyclic alkane or alkene groups comprising one to three heteroatoms selected from the group consisting of O, N, Si and S, and optionally substituted with at least one member selected from the group consisting of Cl, Br, F, I, OH, NH$_2$ and SH;
  (iii) C$_6$ to C$_{25}$ unsubstituted aryl, or C$_6$ to C$_{25}$ unsubstituted heteroaryl, groups having one to three heteroatoms independently selected from the group consisting of O, N, Si and S; and
  (iv) C$_6$ to C$_{25}$ substituted aryl, or C$_6$ to C$_{25}$ substituted heteroaryl, groups having one to three heteroatoms independently selected from the group consisting of O, N, Si and S, and wherein the substituted aryl or substituted heteroaryl group has one to three substituents independently selected from the group consisting of:
    (A) —CH$_3$, C$_2$H$_5$, or C$_3$ to C$_{25}$ straight-chain, branched or cyclic alkane or alkene groups, optionally substituted with at least one member selected from the group consisting of Cl, Br, F, I, OH, NH$_2$ and SH,
    (B) OH,
    (C) NH$_2$, and
    (D) SH; and
  (v) —(CH$_2$)$_n$Si(CH$_2$)$_m$CH$_3$, (CH$_2$)$_n$Si(CH$_3$)$_3$, (CH$_2$)$_n$OSi(CH$_3$)$_m$, where n is independently 1-4 and m is independently 0-4; and
(c) optionally, at least two of R$^1$, R$^2$, R$^3$, R$^4$, R$^5$, R$^6$, R$^7$, R$^1$, R$^9$, and R$^{10}$ can together form a cyclic or bicyclic alkyl or alkenyl group.

In embodiments, the ionic liquid comprises a cation selected from one or more members of the group consisting of pyridinium, pyridazinium, pyrimidinium, pyrazinium, imidazolium, pyrazolium, thiazolium, oxazolium, triazolium, phosphonium, ammonium, benzyltrimethylammonium, choline, cholinium, dimethylimidazolium, guanidinium, phosphonium choline, lactam, sulfonium, tetramethylammonium, and tetramethylphosphonium.

In embodiments, the ionic liquid comprises a non-fluorinated cation (which may be any of the cations above provided fluorine is not present). In embodiments, the ionic liquid comprises a non-halogenated cation (which may be any of the cations above provided a halogen is not present.)

In embodiments, the ionic liquid comprises an anion selected from one or more members of the group consisting of: [CH$_3$CO$_2$]$^-$, [HSO$_4$]$^-$, [CH$_3$OSO$_3$]$^-$, [C$_2$H$_5$OSO$_3$]$^-$, [CH$_3$C$_6$H$_4$SO$_3$]$^-$ ([TSO]$^-$), [AlCl$_4$]$^-$, [Al$_2$Cl$_7$]$^-$, [ZnCl$_4$]$^{2-}$, [Zn$_2$Cl$_6$]$^{2-}$, [Zn$_3$Cl$_8$]$^{2-}$, [FeCl$_4$]$^-$, [GaCl$_4$]$^-$, [Ga$_2$Cl$_7$]$^-$, [InCl$_4$]$^-$, [In$_2$Cl$_7$]$^-$, [CO$_3$]$^{2-}$, [HCO$_3$]$^-$, [NO$_2$]$^-$, [NO$_3$]$^-$, [SO$_4$]$^{2-}$, [PO$_3$]$^{3-}$, [HPO$_3$]$^{2-}$, [H$_2$PO$_3$]$^{1-}$, [PO$_4$]$^{3-}$, [HPO$_4$]$^{2-}$, [H$_2$PO$_4$]$^-$, [HSO$_3$]$^-$, [CuCl$_2$]$^-$, Cl$^-$, Br$^-$, I$^-$, SCN$^-$, carborates optionally substituted with alkyl or substituted alkyl; and carboranes optionally substituted with alkylamine, substituted alkylamine, alkyl or substituted alkyl.

In embodiments, the ionic liquid comprises an anion selected from one or more members of the group consisting of aminoacetate, ascorbate, benzoate, catecholate, citrate, dimethylphosphate, formate, fumarate, gallate, glycolate, glyoxylate, iminodiacetate, isobutyrate, kojate, lactate, levulinate, oxalate, pivalate, propionate, pyruvate, salicylate, succinamate, succinate, tiglate, tropolonate, [CH$_3$CO$_2$]$^-$, [HSO$_4$]$^-$, [CH$_3$SO$_3$]$^-$, [CH$_3$OSO$_3$]$^-$, [C$_2$H$_5$OSO$_3$]$^-$, [CH$_3$C$_6$H$_4$SO$_3$]$^-$, [AlCl$_4$]$^-$, [Al$_2$Cl$_7$]$^-$, [ZnCl$_4$]$^{2-}$, [Zn$_2$Cl$_6$]$^{2-}$, [Zn$_3$Cl$_8$]$^{2-}$, [FeCl$_4$]$^-$, [GaCl$_4$]$^-$, [Ga$_2$Cl$_7$]$^-$, [InCl$_4$]$^-$, [In$_2$Cl$_7$]$^-$, [CO$_3$]$^{2-}$, [HCO$_3$]$^-$, [NO$_2$]$^-$, [NO$_3$]$^-$, [SO$_4$]$^{2-}$, [PO$_3$]$^{3-}$, [HPO$_4$]$^{2-}$, [H$_2$PO$_4$]$^-$, [HSO$_3$]$^-$, [CuCl$_2$]$^-$, Cl$^-$, Br$^-$, I$^-$, SCN$^-$, [N(CN)$_2$], and anions represented by the structure of the following formula, [R$_1$COO]$^-$, wherein R$^1$ is selected from the group consisting of:
  (i) —CH$_3$, —C$_2$H$_5$, or C$_3$ to C$_{10}$ straight-chain, branched or cyclic alkane or alkene groups, optionally substituted with at least one member selected from the group consisting of Cl, Br, I, OH, NH$_2$ and SH;
  (ii) —CH$_3$, —C$_2$H$_5$, or C$_3$ to C$_{10}$ straight-chain, branched or cyclic alkane or alkene groups that contain one to three heteroatoms selected from the group consisting of O, N, Si and S, and are optionally substituted with at least one member selected from the group consisting of Cl, Br, I, OH, NH$_2$ and SH;
  (iii) C$_6$ to C$_{10}$ unsubstituted aryl, or C$_6$ to C$_{10}$ unsubstituted heteroaryl, groups having one to three heteroatoms independently selected from the group consisting of O, N, Si and S; and
  (iv) C$_6$ to C$_{10}$ substituted aryl, or C$_6$ to C$_{10}$ substituted heteroaryl, groups having one to three heteroatoms independently selected from the group consisting of O, N, Si and S; and wherein the substituted aryl or substituted heteroaryl group has one to three substituents independently selected from the group consisting of:
    (A) —CH$_3$, —C$_2$H$_5$, or C$_3$ to C$_{10}$ straight-chain, branched or cyclic alkane or alkene groups, optionally substituted with at least one member selected from the group consisting of Cl, Br, I, OH, NH$_2$ and SH,
    (B) OH,
    (C) NH$_2$, and
    (D) SH.

The anion of the ionic liquid may be a sulfonate. The sulfonate may have the formula [R—SO$_3$]$^-$, wherein R is an alkyl group or an aryl group. The alkyl group may be a linear alkyl group in which the number of carbons may range from, e.g., 1 to 12. The alkyl group may be unsubstituted, by which it is meant the alkyl group contains only carbon and hydrogen and no heteroatoms. The alkyl group may be substituted, by which it is meant an unsubstituted alkyl group in which one or more bonds to a carbon(s) or hydrogen(s) are replaced by a bond to non-hydrogen and non-carbon atoms. Non-hydrogen and non-carbon atoms include, e.g., a halogen atom other than F. Aryl groups may be unsubstituted or substituted as described above with respect to alkyl groups. However, substituted aryl groups also refer to an unsubstituted monocyclic aryl group in which one or more carbon atoms are bonded to an alkane. The alkane may be linear, have various numbers of carbon, and may be unsubstituted or substituted as described above with respect to alkyl groups.

Figure 2:
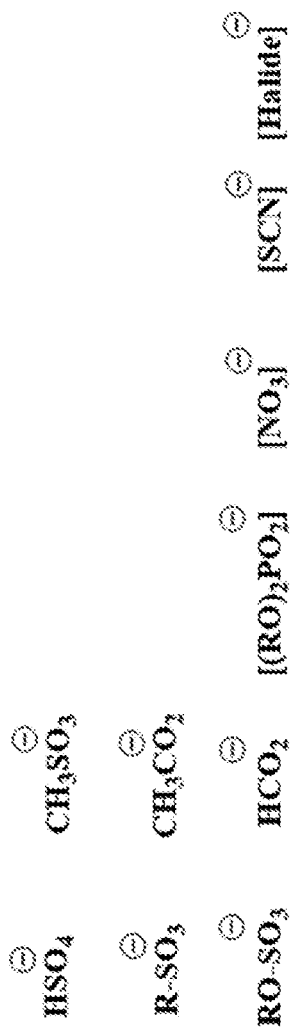
FIG. 2 shows illustrative anions which may be used to form an ionic liquid for use in the present processes.

The anion may be a carboxylate. The carboxylate may have the formula $[R—CO_2]^-$, wherein R is an alkyl group as described above with respect to sulfonate. The carboxylate may be a dicarboxylate, a tricarboxylate, a tetracarboxylate, etc. Other anions which may be used include $[HSO_4]^-$, dicyanamide; and a halide other than fluoride such as Cl, Br, I. Illustrative anions are shown in FIG. 2.

In embodiments, the ionic liquid comprises a non-halogenated anion (which may be any of the anions above provided a halogen is not present).

In embodiments, the ionic liquid is non-fluorinated (i.e., both cation(s) and anion(s) are free of fluorine. In embodiments, the ionic liquid is non-halogenated (i.e., both cation(s) and anion(s) are free of a halogen).

In the present process, the temperature and pressure may be selected to maximize absorption of one of the (hydro)fluorocarbons of the azeotropic mixture in the selected ionic liquid as compared to another one of the (hydro)fluorocarbons. The exposure step forms a (hydro)fluorocarbon-containing ionic liquid (having the greater amount of one of the (hydro)fluorocarbons) and a processed azeotropic mixture (having a corresponding decreased amount of the absorbed (hydro)fluorocarbon). The (hydro)fluorocarbon-containing ionic liquid may be collected. The ionic liquid may be recovered from the (hydro)fluorocarbon-containing ionic liquid and if desired, reused. The processed azeotropic mixture may be exposed to an additional amount of the ionic liquid in order to extract more of the more soluble (hydro)fluorocarbon in the processed azeotropic mixture. These collection steps and additional ionic liquid exposure steps may be repeated as desired. A variety of extractive distillation systems may be used to carry out the disclosed methods. These systems and their use are generally known.

The disclosed processes may allow the different (hydro)fluorocarbons in an azeotropic mixture to be separated from one other to a high degree of purity, e.g., to a purity of greater than 95 mole percent, 97 mole percent, 99 mole percent, or higher.

EXAMPLES

Example 1: Ionic Liquids with Chloride Anion Dictate the Successful Separation of R-410a into R-125 and R-32

The Vapor-Liquid-Equilibria of R-125 and R-32 in three ionic liquids with non-fluorinated anions, i.e., 1-butyl-3-methylimidazolium acetate ($[C_4C_1im][Ac]$), 1-hexyl-3-methylimidazolium chloride ($[C_6C_1im][Cl]$), and 1-butyl-3-methylimidazolium thiocyanate ($[C_4C_1im][SCN]$) at 298.15 K and pressures up to 1.0 MPa were measured using a gravimetric microbalance (Hiden Isochema Ltd., IGA 003, Warrington, United Kingdom). The experimental solubility data (T, p, $w_1$) for R-32 and R-125 in $[C_4C_1im][Ac]$, $[C_4C_1im][SCN]$ and $[C_6C_1im][Cl]$ are summarized in Tables 2-4.

TABLE 2

Experimental Solubility (T, P, $w_1$) data for R-32 (1) and R-125 (1) in $[C_4C_1im][Ac]$ (2) at 298.15K.

| R-32 (1) + $[C_4C_1im][Ac]$ (2) | | R-125 (1) + $[C_4C_1im][Ac]$ (2) | |
|---|---|---|---|
| p (MPa) | $w_1$ (wt. %) | p (MPa) | $w_1$ (wt. %) |
| 0.050 | 1.5 | 0.050 | 3.7 |
| 0.100 | 2.7 | 0.100 | 7.7 |
| 0.200 | 4.8 | 0.200 | 16.0 |
| 0.400 | 8.7 | 0.400 | 31.0 |
| 0.600 | 12.6 | 0.599 | 40.8 |
| 0.800 | 16.8 | 0.799 | 49.1 |
| 1.000 | 21.2 | 1.000 | 56.9 |

TABLE 3

Experimental Solubility (T, P, $w_1$) data for R-32 (1) and R-125 (1) in $[C_4C_1im][SCN]$ (2) at 298.15K.

| R-32 (1) + $[C_4C_1im][SCN]$ (2) | | R-125 (1) + $[C_4C_1im][SCN]$ (2) | |
|---|---|---|---|
| p (MPa) | $w_1$ (wt. %) | p (MPa) | $w_1$ (wt. %) |
| 0.050 | 0.1 | 0.050 | 0.0 |
| 0.100 | 0.6 | 0.100 | 0.3 |
| 0.200 | 1.6 | 0.200 | 0.8 |
| 0.400 | 3.7 | 0.400 | 1.9 |
| 0.600 | 6.6 | 0.599 | 3.2 |
| 0.800 | 9.3 | 0.799 | 4.7 |
| 1.000 | 12.4 | 1.000 | 6.5 |

TABLE 4

Experimental Solubility (T, P, $w_1$) data for R-32 (1) and R-125 (1) in $[C_6C_1im][Cl]$ (2) at 298.15K.

| R-32 (1) + $[C_6C_1im][Cl]$ (2) | | R-125 (1) + $[C_6C_1im][Cl]$ (2) | |
|---|---|---|---|
| p (MPa) | $w_1$ (wt. %) | p (MPa) | $w_1$ (wt. %) |
| 0.050 | 0.5 | 0.050 | 2.4 |
| 0.100 | 1.2 | 0.100 | 4.8 |
| 0.200 | 2.5 | 0.200 | 10.2 |
| 0.400 | 5.6 | 0.400 | 19.5 |
| 0.600 | 8.8 | 0.599 | 29.6 |
| 0.800 | 11.9 | 0.799 | 41.3 |
| 1.000 | 15.2 | 1.000 | 52.9 |

The P, T, $w_1$ data presented in Tables 2-4 show that the solubility of both R-32 and R-125 increases with increasing pressure. However, it is the large quantities of either R-32 or R-125 that can be dissolved in an ionic liquid that makes such a binary system particularly useful for the separation of gas mixtures. For instance, R-125 is 3.4-fold more soluble than R-32 in $[C_6C_1im][Cl]$, while in $[C_4C_1im][Ac]$ R-125 is only 2.6-fold more soluble than R-32.

Interestingly, R-125 is much more soluble in $[C_6C_1im][Cl]$ and $[C_4C_1im][Ac]$ than in $[C_4C_1im][SCN]$. These solubility measurements show that gas solubilities in ionic liquids depend primarily on the strength of interaction of the gas with the anion.

Example 2: Ionic Liquids with Fluorinated Anions do not Maximize the Separation of R-410a into R-125 and R-32

The Vapor-Liquid-Equilibria of R-125 and R-32 in two ionic liquids with fluorinated anions, i.e., 1-butyl-3-methylimidazolium tetrafluoroborate [$C_4C_1$im][$BF_4$] and 1-butyl-3-methylimidazolium hexafluorophosphate [$C_4C_1$im][$PF_6$] at 298.15 K and pressures up to 1.0 MPa were measured using a gravimetric microbalance. The experimental solubility data (T, p, $w_1$) for R-32 and R-125 in [$C_4C_1$im][$BF_4$] and [$C_4C_1$im][$PF_6$] are summarized in Tables 5-6.

TABLE 5

Experimental Solubility (T, P, $w_1$) data for R-32 (1) and R-125 (1) in [$C_4C_1$im][$BF_4$] (2) at 298.15K.

| R-32 (1) + [$C_4C_1$im][$BF_4$] (2) | | R-125 (1) + [$C_4C_1$im][$BF_4$] (2) | |
|---|---|---|---|
| p (MPa) | $w_1$ (wt. %) | p (MPa) | $w_1$ (wt. %) |
| 0.050 | 0.6 | 0.050 | 0 |
| 0.100 | 1.4 | 0.100 | 1.0 |
| 0.200 | 3.1 | 0.200 | 2.3 |
| 0.400 | 6.8 | 0.400 | 5.6 |
| 0.600 | 11.8 | 0.599 | 10.0 |
| 0.800 | 15.8 | 0.799 | 15.9 |
| 1.000 | 21.9 | 1.000 | 24.4 |

TABLE 6

Experimental Solubility (T, P, $w_1$) data for R-32 (1) and R-125 (1) in [$C_4C_1$im][$PF_6$] (2) at 298.15K.

| R-32 (1) + [$C_4C_1$im][$PF_6$] (2) | | R-125 (1) + [$C_4C_1$im][$PF_6$] (2) | |
|---|---|---|---|
| p (MPa) | $w_1$ (wt. %) | p (MPa) | $w_1$ (wt. %) |
| 0.050 | 0.7 | 0.050 | 0.5 |
| 0.100 | 1.5 | 0.100 | 1.0 |
| 0.200 | 3.0 | 0.200 | 2.1 |
| 0.400 | 6.4 | 0.400 | 4.4 |
| 0.600 | 10.3 | 0.599 | 7.2 |
| 0.800 | 14.6 | 0.799 | 11.0 |
| 1.000 | 19.8 | 1.000 | 16.1 |

It is most striking that R-32 is more soluble than R-125 in [$C_4C_1$im][$BF_4$] and [$C_4C_1$im][$PF_6$], which is the opposite trend found for [$C_6C_1$im][Cl], and much smaller differences in solubility were observed. For example, R-125 is 3.4-fold more soluble than R-32 in [$C_6C_1$im][Cl], while R-32 is more soluble than R-125 in [$C_4C_1$im][$BF_4$] at 298.15 K and 0.1 MPa.

Example 3: Separation of Azeotropic Hydrofluorocarbon Mixture R-410a Using Ionic Liquids Introduction Hydrofluorocarbons (HFCs) are a family of refrigerants extensively used in air-conditioning and refrigeration systems. HFCs were developed to replace chlorofluorocarbons that were linked to the depletion of the Earth's ozone layer. HFCs have zero ozone depletion potential (ODP), but some have high global warming potential (GWP). The Kyoto Protocol of the United Nations Framework Convention on Climate Change (UNFCCC) has recommended the phase-out of HFCs under the Kigali Amendment to the Montreal Protocol. In addition, the EU Regulation No. 517/2014, which mandates the reduction of up to two thirds of the 2010 fluorinated greenhouse gas (GHG) emissions by 2030, has been implemented.

R-410A is a near-azeotropic HFC mixture composed of 50.0 mass % HFC-32 ($CH_2F_2$, Normal Boiling Point Temperature (NBPT)=221.3 K) and 50.0 mass % HFC-125 ($CHF_2CF_3$, NBPT=224.9 K) that was developed as a replacement for HCFC-22 ($CHClF_2$) in residential and commercial air-conditioning and heat pump systems. Currently there is no commercial technology available for separation of HFC-32 and HFC-125; therefore, if R-410A cannot be recycled in the future it will have to be incinerated. The need for a sustainable process to separate R-410A such that HFC-32 can be used in low-GWP blends with hydrofluoroolefins (HFOs) and HFC-125 can be utilized as a feedstock for future products is critically important considering the pending and new regulations that will limit the use of HFCs.

In this example, the vapor-liquid equilibria (single-component absorption) of the R-410A components, i.e., HFC-32 and HFC-125, in 1-butyl-3-methylimidazolium acetate ([$C_4C_1$im][$C_1CO_2$]), [$C_4C_1$im][$BF_4$], [$C_4C_1$im][$PF_6$], 1-butyl-3-methylimidazolium thiocyanate ([$C_4C_1$im][SCN]), 1-hexyl-3-methylimidazolium chloride ([$C_6C_1$im][Cl]), and 1-hexyl-3-methylimidazolium tris(pentafluoroethyl)trifluorophosphate ([$C_6C_1$im][FAP]), were measured using a gravimetric microbalance at 298.15 K and pressures up to 1.0 MPa. The van der Waals Equation of State (EoS) model was applied to correlate and predict the phase equilibria for each HFC-32/IL and HFC-125/IL mixture using the experimental solubility data. In addition, the time-dependent behavior of the HFC/IL systems was analyzed using the one-dimensional Fick's law. Finally, the ideal selectivity of the separation of R-410A for each IL was calculated by taking the ratio of the Henry's law constants at 298.15 K and the ratio of the mass absorption at 1.0 MPa and 298.15 K.

Materials and Methods

Materials

Figure 3:
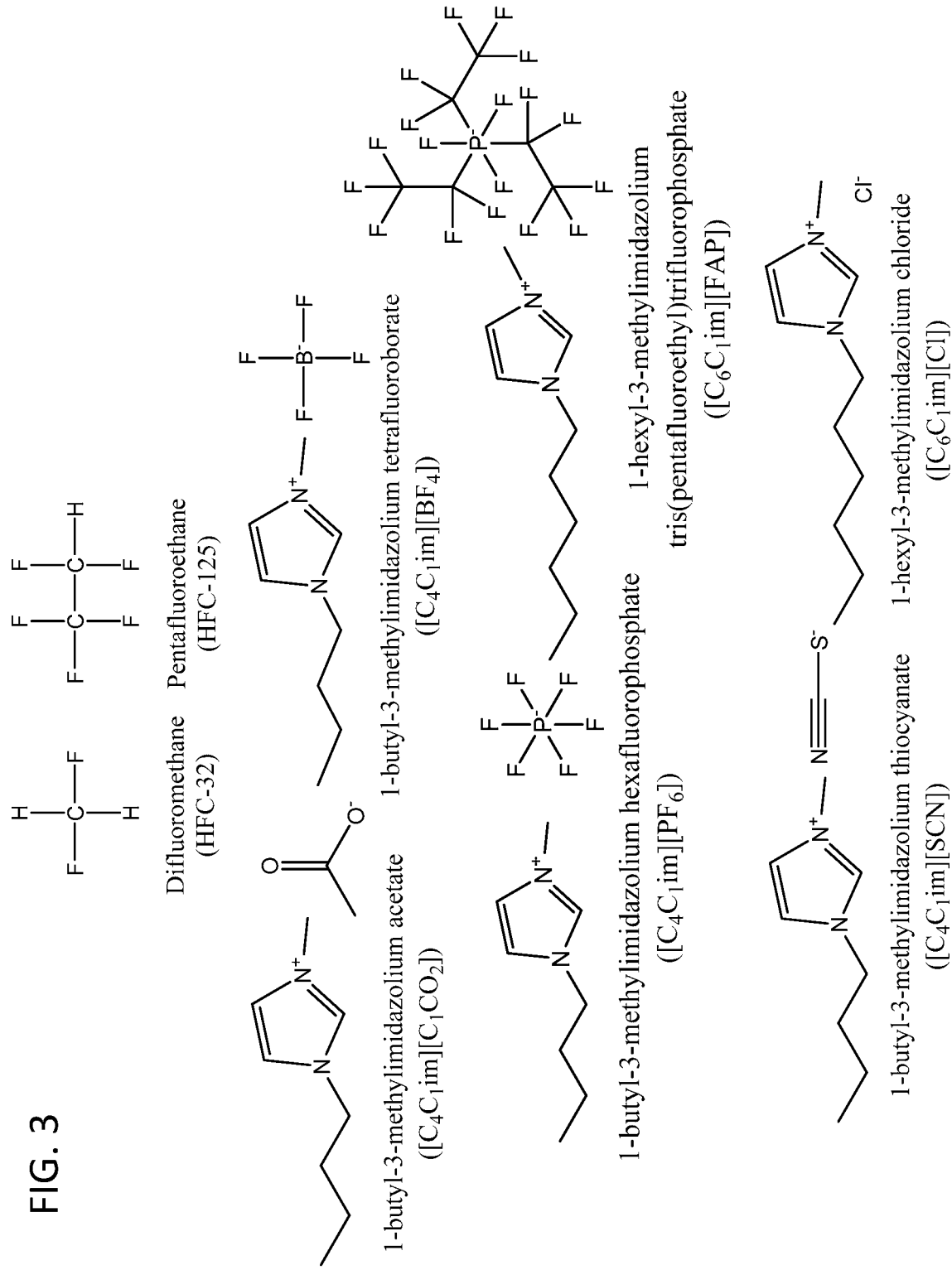
FIG. 3 shows chemical structures and acronyms of the HFC refrigerants and ILs.

HFC-32 (CAS #75-10-5) and HFC-125 (CAS #354-33-6) were obtained from The Chemours Company (Newark, DE) with a minimum purity of 99.9 wt %, and used as received. Ionic liquids were purchased from commercial suppliers as follows: [$C_4C_1$im][$C_1CO_2$] (assay, ≥95 wt %, CAS No. 284049-75-8, Lot and Filling Code S25803 444041302), [$C_4C_1$im][$BF_4$] (assay, ≥97 wt %, CAS No. 174501-65-6, Lot and Filling Code No. 1116280 23404335), [$C_4C_1$im][$PF_6$] (assay, ≥96 wt %, CAS No. 174501-64-5, Lot and Filling Code No. 1242554 304070904), [$C_4C_1$im][SCN] (assay, ≥95 wt %, CAS No. 344790-87-0, Lot and Filling code, S25812 14804B3), and [$C_6C_1$im][Cl] (assay, ≥97 wt %, CAS No. 171058-17-6, Lot and Filling code, 1086333 41705081) were obtained from the Fluka Chemika (Switzerland). [$C_6C_1$im][FAP] (assay, ≥99 wt %, CAS No. 713512-19-7, Lot and Filling code, S4872378 733) was purchased from EMD Millipore, Inc. (United States). The densities of HFC-32 and HFC-125 were obtained from the National Institute of Standards and Technology (NIST) REFPROP V.10.0 database. (Lemmon, E. W. et al., *NIST Reference Fluid Thermodynamic and Transport Properties—REFPROP* 10.0, Gaithersburg, Maryland, 2013.) The densities and molecular weight of the ILs were obtained from the literature. (Shiflett, M. B. et al., *AIChE J.* 2006, 52, (3), 1205-1219; and Shiflett, M. B. et al., *Fluid Phase Equilibr.* 2006, 242, (2), 220-232.) FIG. 3 provides the chemical structures and acronyms for the HFC refrigerants and ILs studied in this example.

Experimental Methodology

The gas absorption measurements were performed using a gravimetric microbalance (Hiden Isochema Ltd., IGA 003, Warrington, United Kingdom). The experimental equipment and protocols for the gas solubility measurements have been described in detail previously; therefore, only a brief description is provided here. (Shiflett et al., 2006.) Approximately 50 mg of IL was loaded in a flat bottom Pyrex sample container and degassed under vacuum ($10^{-10}$ MPa) at 348.15 K for 12 hours to remove any trace amounts of water and/or other volatile impurities prior to the measurements. To ensure enough time to reach vapor-liquid equilibrium at 298.15 K, each pressure setpoint was held for a minimum of 8 hours. The kinetic sorption profile and balance stability were monitored by the HISorp software program to ensure that the HFC/IL mixtures had reached thermodynamic equilibrium. The gas sorption measurements were performed in "static mode", where set point pressures were maintained constant within the system through simultaneous adjustments in admit and exhaust valves. The sample and counterweight temperatures were measured using an in-situ K-type thermocouple with an uncertainty of 0.1 K. Both temperature and pressure transducers in the microbalance were calibrated using NIST certified reference instruments. The in-situ thermocouple was calibrated using a standard platinum resistance thermometer (Hart Scientific SPRT model 5699 and readout Hart Scientific Blackstack model 1560 with a SPRT module 2560) with an accuracy of ±0.005 K. Pressures under vacuum ($10^{-10}$ to $10^{-5}$ MPa) were measured using a Pfeiffer vacuum gauge (model PKR251) and pressures from vacuum ($10^{-5}$ MPa) to higher pressure (2.0 MPa) were measured using a Druck pressure transducer (model PDCR4010) with an accuracy of ±0.0008 MPa. The IGA microbalance had a mass resolution of 0.0001 mg for absorption and desorption measurements at any given temperature and pressure. The gas sorption data were corrected for buoyancy and volume expansion as previously described. (Minnick, D. L. et al., *J. Vac. Sci. Technol A* 2018, 36, (5).)

Equation of State Modeling

It has been shown that a generic van der Waals EoS accurately predicts solubilities of gases including $CO_2$, $NH_3$, $SO_2$, and hydrofluorocarbons such as HFC-134a, in room temperature ionic liquids (RTILs). (Yokozeki, A. et al., *J Supercrit. Fluids* 2010, 55, (2), 846-851.) In this example, parameters have been fit to the same generic van der Waals model for mixtures of HFC-32 and HFC-125 in the ILs studied. The van der Waals Equation of State (EoS) is modeled by the following equations:

$$P = \frac{RT}{V-b} - \frac{a(T)}{V^2} \quad (1)$$

$$a_i(T) = \frac{0.421875 R^2 T_{Ci}^2 \alpha_i(T)}{P_{Ci}} \quad (2)$$

$$b_i = \frac{0.125 R T_{Ci}}{P_{Ci}} \quad (3)$$

$$\alpha_i(T) = \sum_{k=0}^{\leq 3} \beta_{ki}\left(\frac{1}{T_{ri}} - T_{ri}\right)^k, \quad \left(T_{ri} \equiv \frac{T}{T_{Ci}}\right) \quad (4)$$

where $\alpha$ represents the temperature dependence of the a parameter. The critical constant, $\beta$, the critical temperature, $T_c$, and the critical pressure, $P_c$, for HFC-32 and HFC-125 were obtained from prior calculations by Yokozeki and are shown in Table 7. (Yokozeki, A., *Int. J. Thermophys.* 2001, 22, (4), 1057-1071.)

TABLE 7

| | HFC Critical Parameters | | | | | |
|---|---|---|---|---|---|---|
| Compound | $T_C$ (K) | $P_C$ (kPa) | $\beta_{HFC, A}$ | $\beta_{HFC, B}$ | $\beta_{HFC, C}$ | $\beta_{HFC, D}$ |
| HFC-32 | 351.26 | 5782 | 1.0019 | 0.48333 | −0.07538 | 0.00673 |
| HFC-125 | 339.19 | 3637 | 1.0001 | 0.47736 | −0.01977 | −0.0177 |

The following temperature dependence for the a parameter for ILs has been proposed:

$$\alpha(T) = 1 + \beta_{IL,i}\left(\frac{1}{T_{r,IL}} - T_{r,IL}\right) \quad (5)$$

where $\beta_{IL}$ is an adjustable fitting parameter and calculated for each IL. In this example, the $T_c$ and $P_c$ used for all ILs were set to 1000 K and 2.5 MPa. The model fit is extremely insensitive to the choice of IL $T_c$ and $P_c$ as shown below.

The following mixing rules were originally developed for refrigerant-lubricant mixtures involving large molecular-size differences and/or asymmetric interactions with respect to compositions and were extended to refrigerant/ionic liquid mixtures:

$$a = \sum_{i,j=1}^{N} \sqrt{a_i a_j}\, f_{ij}(T)(1 - k_{ij}) x_i x_j \quad (6)$$

$$f_{ij}(T) = 1 + \frac{\tau_{ij}}{T} \quad (7)$$

$$k_{ij} = \frac{l_{ij} l_{ji}(x_i + x_j)}{l_{ji} x_i + l_{ij} x_j} \quad \text{where } k_{ii} = 0 \quad (8)$$

$$b = 0.5 \sum_{i,j=1}^{N}(b_i + b_j)(1 - k_{ij})(1 - m_{ij}) x_i x_j \quad (9)$$

Here l, m, and τ are binary interaction parmeters, $x_i$ is the mole fraction of species i, and R is the universal gas constant. It is assumed $l_{ii}=l_{jj}=1$, $m_{ij}=m_{ji}$ and $m_{ii}=0$, and $\tau_{ij}=\tau_{ji}$ and $\tau_{ii}=0$, which leaves only four of these parameters ($l_{ij}$, $l_{ji}$, $m_{ij}$, and $\tau_{ij}$) to be estimated via nonlinear regression.

With $\beta_{IL}$ and the four binary interaction parameters, five total parameters were fit in this model. Many combinations for the parameters $l_{ij}$, $l_{ji}$ m, τ, and $\beta_{IL}$ are possible for which the model predictions closely match the experimental data; therefore, the choice of binary interaction parameters has negligible impact on the quality of the fit.

The fugacity coefficient is defined as:

$$\ln \phi_i = \ln\left(\frac{RT}{P(V-b)}\right) + \frac{b'_i}{V-b} - \frac{a'_i + a}{VRT} \quad (10)$$

where, $$a'_i = 2\sum_{j=1}^{N} \sqrt{a_i a_j}\, f_{ij} x_j \left\{ 1 - k_{ij} - \frac{l_{ij} l_{ji}(l_{ij} - l_{ji}) x_i x_j}{(l_{ji} x_i + l_{ij} x_j)^2} \right\} - a \quad (11)$$

$$b'_i = \sum_{j=1}^{N} (b_i + b_j)(1 - m_{ij}) x_j \left\{ 1 - k_{ij} - \frac{l_{ij} l_{ji}(l_{ij} - l_{ji}) x_i x_j}{(l_{ji} x_i + l_{ij} x_j)^2} \right\} - b \quad (12)$$

and equilibria between the liquid and vapor phases is determined by:

$$(x_i \phi_i)^L = (y_i \phi_i)^V \quad (13)$$

The amount of IL in the vapor phase is assumed to be zero, due to the negligible vapor pressure of ILs; therefore, the vapor mole fraction of HFC is unity ($y_{HFC}=1$) and its phase equilibria is modeled by:

$$x_{HFC} \phi_{HFC}^L = \phi_{HFC}^V \quad (14)$$

To fit the ionic liquid critical parameter and binary interaction parameters for each mixture, nonlinear regression was used to solve the following:

$$\min_{l_{ij}, l_{ji}, m, \tau, \beta_{IL}} (P_{vdW} - P_{exp})^2 \quad (15)$$

constrained by Equations (1)-(14) to calculate $P_{vdW}$. $P_{exp}$ are the experimentally measured pressures at equilibrium.

Henry's Law Constant at Infinite Dilution

Henry's law constants ($k_H$) were used to evaluate the refrigerant absorption in ILs at infinite dilution concentrations, where lower $k_H$ values indicate higher refrigerant solubility in the solvent. (Shiflett, M. B. et al., *Ind. Eng. Chem. Res.* 2006, 45, (18), 6375-6382.) In this example, both HFC-32 and HFC-125 solubilities increase linearly with increasing pressure up to about 0.2 MPa, indicating the Henry's law regime; therefore, the refrigerant partial pressure was directly proportional to its liquid composition in the liquid phase, under dilute conditions. The Henry's law constant can be calculated from experimental refrigerant solubility (PTx) data assuming the hydrostatic pressure correction (Krichevsky-Kasarnovsky equation) is not required:

$$k_H = \lim_{x_1 \to 0} \frac{f_1^V(T, P, y_1)}{x_1} \approx \left(\frac{df_1^V}{dx_1}\right)_{x_1=0} \quad (16)$$

where $f_1^V$ is the vapor phase fugacity of HFC-32 and HFC-125 ($y_1=1$) absorbed in the IL, which was calculated using an EoS model at given temperature and pressure. (Lemmon, E. W. et al., 2013.) The Henry's law constants were calculated by determining the slope of a linear regression, fitting the experimental solubility data up to about 0.2 MPa, including the theoretical point with no refrigerant in the IL at zero pressure.

Fickian Diffusion Analysis

In addition to the equilibrium solubility, the time-dependent absorption data for HFC-32 and HFC-125 in the ILs were also measured using the gravimetric microbalance at 298.15 K and pressures ranging from 0.05 to 1.0 MPa. Details on how to apply Fick's law to the current physical situation have been previously reported; therefore, only a few important assumptions and conditions will be provided here. (Minnick, D. L. et al., 2018.) In this simplified Fickian diffusion model, the following assumptions for the dissolving refrigerant in IL were applied: (i) the interactions between the HFC and IL are physical; (ii) HFC dissolves through a one-dimensional (vertical) diffusion process, and there is no convective flow in the IL; (iii) a thin boundary layer exists between HFC and IL at given T and P, where the thermodynamic equilibrium is established with the saturation concentration (Cs); (iv) HFC/IL mixture is a dilute solution, and thermophysical properties do not change at given T and P. (Shiflett, M. B. et al., 2006.) These assumptions allow describing the dissolution of the HFC in ILs based on the one-dimensional mass diffusion, due to local concentration difference:

$$\frac{\partial C}{\partial t} = D \frac{\partial^2 C}{\partial z^2} \quad (17)$$

Initial Condition:

$$t=0, 0 < z < L, \text{and } C = C_0 \quad (18)$$

Boundary Conditions (i and ii):

$$(i)\ t > 0,\ z = 0,\ \text{and } C = C_S \quad (19)$$

$$(ii)\ t > 0,\ z = L,\ \text{and } \frac{\partial C}{\partial z} = 0 \quad (20)$$

where C is the concentration of the HFC in the IL as a function of time (t), z is the vertical location, z=0 corresponds to the vapor-liquid boundary, L is the depth of the IL in the sample container, and D is the diffusion coefficient that was assumed to be constant. The depth (L) was estimated by knowing the cylindrical geometry of the sample container, mass, and average weight fraction density of the HFC/IL mixture at initial ($C_0$) and saturation concentration ($C_s$) at a given T and P. Equation 17 was solved analytically by applying the proper initial and boundary conditions (Equations 18-20), and the separation of variables or Laplace transform methods to yield the following: (Yokozeki, A., *Int. J. Refrig.* 2002, 25, (6), 695-704.)

$$<C> = C_s \left[ 1 - 2\left(1 - \frac{C_0}{C_s}\right) \sum_{n=0}^{\infty} \frac{\exp(-\lambda_n^2 D t)}{L^2 \lambda_n^2} \right] \quad (21)$$

where $\lambda_n = [n + (1/2)](\pi/L)$.

Although Equation 21 has an infinite summation term, only the first ten terms were applied in this analysis. The diffusion coefficient (D) and solubility limit at equilibrium ($C_s$) for each HFC in IL data set were calculated through nonlinear regression of Equation 21 using MATLAB software, and the best model fit was obtained by selecting the proper $C_0$ value.

Results and Discussion

Vapor Liquid Equilibrium Results

Figure 4:
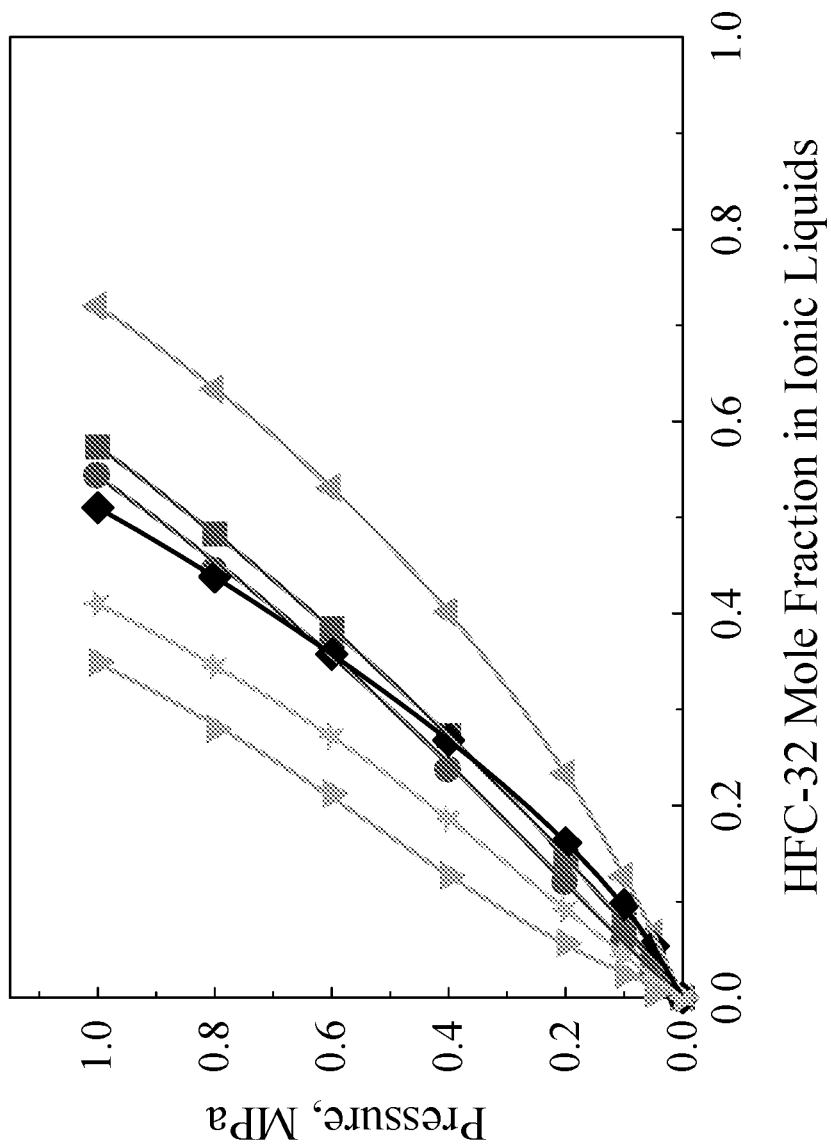
FIG. 4 shows Vapor-liquid equilibrium (VLE) data for HFC-32 in $[C_4C_1im][SCN](\blacktriangledown)$, $[C_6C_1im][Cl](\star)$, $[C_4C_1im][C_1CO_2](\blacklozenge)$, $[C_4C_1im][BF_4](\bullet)$, $[C_4C_1im][PF_6]$ ($\blacksquare$), and $[C_6C_1im][FAP](\blacktriangle)$ at 298.15 K. Symbols are measured experimental data (PTx) and lines are van der Waals EoS model predictions.
Figure 5:
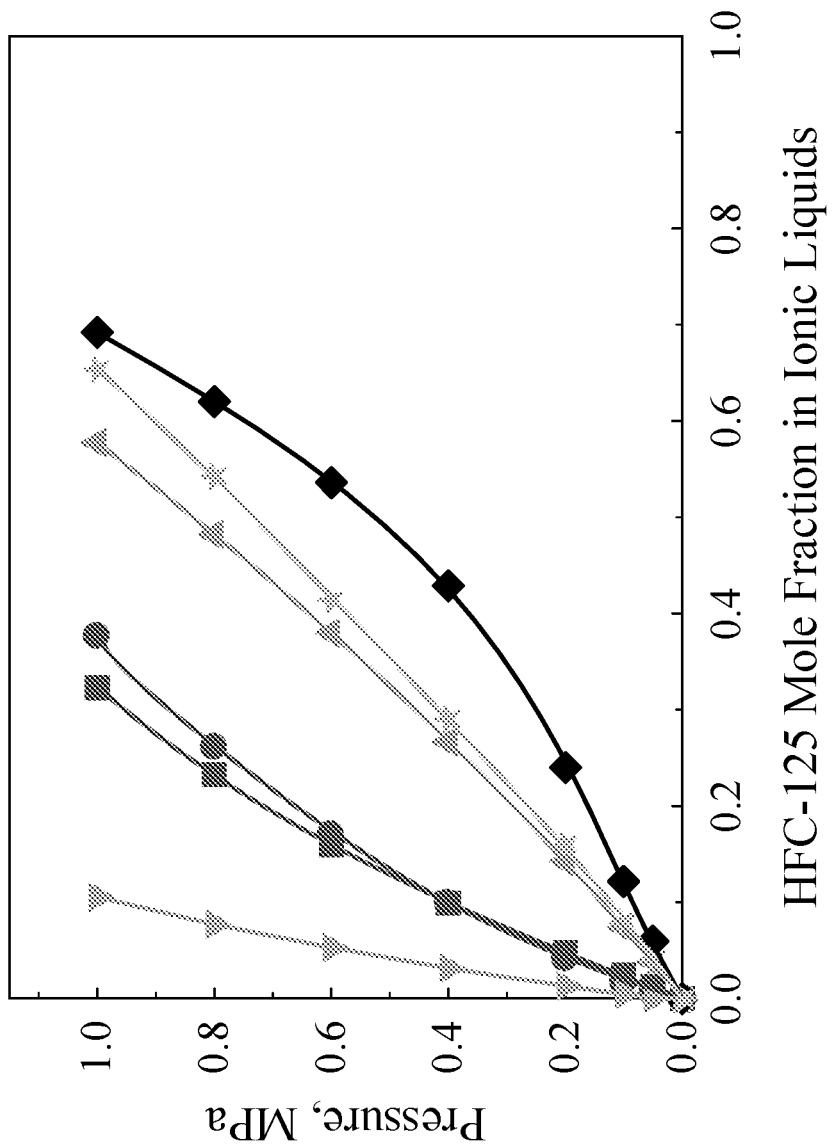
FIG. 5 shows VLE for HFC-125 in $[C_4C_1im][SCN](\blacktriangledown)$, $[C_4C_1im][PF_6](\blacksquare)$, $[C_4C_1im][BF_4](\bullet)$, $[C_6C_1im][FAP](\blacktriangle)$, $[C_6C_1im][Cl](\star)$, and $[C_4C_1im][C_1CO_2](\blacklozenge)$ at 298.15 K. Symbols are measured experimental data (PTx) and solid lines are van der Waals EoS model predictions.

HFC solubility in ILs depends on the interaction strength between the refrigerant and the IL anion. For instance, the relatively high solubility of HFC-32 in ILs containing fluorinated anions is thought to be due to hydrogen bonding between the hydrogen on the refrigerant and the fluorine on the anion. Large solubility differences for HFC-32 relative to HFC-125 in [$C_4C_1$im][$PF_6$] have also been found. Specifically, HFC-32/[$C_4C_1$im][$PF_6$] had a Henry's law constant of 8.8±0.7 bar, while HFC-125/[$C_4C_1$im][$PF_6$] had a Henry's law constant of 23.1±2.3 bar at 298.15 K. In this example, experimental solubility data of HFC-32 and HFC-125 in three ILs with fluorinated anions ([$C_4C_1$im][$BF_4$], [$C_4C_1$im][$PF_6$], and [$C_6C_1$im][FAP]) and in three ILs with non-fluorinated anions ([$C_4C_1$im][$C_1CO_2$], [$C_4C_1$im][SCN], and [$C_6C_1$im][Cl]) at pressures ranging from 0.05 to 1.0 MPa and at 298.15 K were measured (Tables 8 to 13) and correlated using the van der Waals EoS model as shown in FIG. 4 and FIG. 5.

TABLE 8

Experimental VLE for HFC-32/[$C_4C_1$im][$BF_4$] and HFC-125/[$C_4C_1$im][$BF_4$] mixtures at 298.15K.

| HFC-32 (1) + [$C_4C_1$im][$BF_4$] (2) | | | HFC-125 (1) + [$C_4C_1$im][$BF_4$] (2) | | |
|---|---|---|---|---|---|
| P (MPa) | $100x_1$ (mol %) | $w_1$ (wt %) | P (MPa) | $100x_1$ (mol %) | $w_1$ (wt %) |
| 0.05 | 2.4 | 0.6 | 0.05 | 0.8 | 0.4 |
| 0.1 | 5.8 | 1.4 | 0.1 | 1.9 | 1.0 |
| 0.2 | 12.2 | 3.1 | 0.2 | 4.3 | 2.3 |
| 0.4 | 23.9 | 6.8 | 0.4 | 10.1 | 5.6 |
| 0.6 | 36.5 | 11.8 | 0.6 | 17.2 | 10.0 |
| 0.8 | 44.6 | 15.8 | 0.8 | 26.3 | 15.9 |
| 1.0 | 54.5 | 21.9 | 1.0 | 37.8 | 24.4 |

P—Pressure; $100x_1$ and $w_1$ - HFC composition (mol % and wt %) in IL.
Standard uncertainties: u(T) = 0.1° C.; u(P) = 0.0008 MPa and u($100x_1$) = 0.5 mol %.

TABLE 9

Experimental VLE for HFC-32/[$C_4C_1$im][$PF_6$] and HFC-125/[$C_4C_1$im][$PF_6$] mixtures at 298.15K.

| HFC-32 (1) + [$C_4C_1$im][$PF_6$] (2) | | | HFC-125 (1) + [$C_4C_1$im][$PF_6$] (2) | | |
|---|---|---|---|---|---|
| P (MPa) | $100x_1$ (mol %) | $w_1$ (wt %) | P (MPa) | $100x_1$ (mol %) | $w_1$ (wt %) |
| 0.05 | 3.9 | 0.7 | 0.05 | 1.2 | 0.5 |
| 0.1 | 7.6 | 1.5 | 0.1 | 2.4 | 1.0 |
| 0.2 | 14.6 | 3.0 | 0.2 | 4.8 | 2.1 |
| 0.4 | 27.3 | 6.4 | 0.4 | 9.9 | 4.4 |
| 0.6 | 38.4 | 10.2 | 0.6 | 16.0 | 7.2 |
| 0.8 | 48.3 | 14.6 | 0.8 | 23.2 | 11.0 |
| 1.0 | 57.4 | 19.8 | 1.0 | 32.3 | 16.1 |

P—Pressure; $100x_1$ and $w_1$ - HFC composition (mol % and wt %) in IL.
Standard uncertainties: u(T) = 0.1° C.; u(P) = 0.0008 MPa and u($100x_1$) = 0.5 mol %.

TABLE 10

Experimental VLE for HFC-32/[$C_6C_1$im][FAP] and HFC-125/[$C_6C_1$im][FAP] mixtures at 298.15K.

| HFC-32 (1) + [$C_6C_1$im][FAP] (2) | | | HFC-125 (1) + [$C_6C_1$im][FAP] (2) | | |
|---|---|---|---|---|---|
| P (MPa) | $100x_1$ (mol %) | $w_1$ (wt %) | P (MPa) | $100x_1$ (mol %) | $w_1$ (wt %) |
| 0.05 | 6.7 | 0.6 | 0.05 | 3.8 | 0.8 |
| 0.1 | 12.6 | 1.2 | 0.1 | 7.4 | 1.5 |
| 0.2 | 23.3 | 2.5 | 0.2 | 14.2 | 3.1 |
| 0.4 | 40.2 | 5.4 | 0.4 | 26.7 | 6.6 |
| 0.6 | 53.1 | 8.8 | 0.6 | 38.0 | 10.7 |
| 0.8 | 63.4 | 12.9 | 0.8 | 48.2 | 15.3 |
| 1.0 | 72.0 | 18.1 | 1.0 | 57.8 | 20.9 |

P—Pressure; $100x_1$ and $w_1$ - HFC composition (mol % and wt %) in IL.
Standard uncertainties: u(T) = 0.1° C.; u(P) = 0.0008 MPa and u($100x_1$) = 0.5 mol %.

TABLE 11

Experimental VLE for HFC-32/[$C_4C_1$im][$C_1CO_2$] and HFC-125/[$C_4C_1$im][$C_1CO_2$] mixtures at 298.15K.

| HFC-32 (1) + [$C_4C_1$im][$C_1CO_2$] (2) | | | HFC-125 (1) + [$C_4C_1$im][$C_1CO_2$] (2) | | |
|---|---|---|---|---|---|
| P (MPa) | $100x_1$ (mol %) | $w_1$ (wt %) | P (MPa) | $100x_1$ (mol %) | $w_1$ (wt %) |
| 0.05 | 5.4 | 1.5 | 0.05 | 6.0 | 3.7 |
| 0.1 | 9.7 | 2.7 | 0.1 | 12.2 | 7.7 |
| 0.2 | 16.1 | 4.8 | 0.2 | 24.0 | 16.0 |
| 0.4 | 26.8 | 8.7 | 0.4 | 42.9 | 31.0 |
| 0.6 | 35.7 | 12.6 | 0.6 | 53.6 | 40.8 |
| 0.8 | 43.8 | 16.8 | 0.8 | 62.0 | 49.1 |
| 1.0 | 51.0 | 21.2 | 1.0 | 69.2 | 56.9 |

P—Pressure; $100x_1$ and $w_1$ - HFC composition (mol % and wt %) in IL.
Standard uncertainties: u(T) = 0.1° C.; u(P) = 0.0008 MPa and u($100x_1$) = 0.5 mol %.

TABLE 12

Experimental VLE for HFC-32/[$C_4C_1$im][SCN] and HFC-125/[$C_4C_1$im][SCN] mixtures at 298.15K.

| HFC-32 (1) + [$C_4C_1$im][SCN] (2) | | | HFC-125 (1) + [$C_4C_1$im][SCN] (2) | | |
|---|---|---|---|---|---|
| P (MPa) | $100x_1$ (mol %) | $w_1$ (wt %) | P (MPa) | $100x_1$ (mol %) | $w_1$ (wt %) |
| 0.05 | 0.4 | 0.1 | 0.05 | <0.1 | <0.1 |
| 0.1 | 2.4 | 0.6 | 0.1 | 0.4 | 0.3 |
| 0.2 | 5.7 | 1.6 | 0.2 | 1.3 | 0.8 |
| 0.4 | 12.7 | 3.7 | 0.4 | 3.1 | 1.9 |
| 0.6 | 21.2 | 6.6 | 0.6 | 5.3 | 3.2 |
| 0.8 | 28.0 | 9.3 | 0.8 | 7.7 | 4.7 |
| 1.0 | 34.9 | 12.4 | 1.0 | 10.5 | 6.5 |

P—Pressure; $100x_1$ and $w_1$ - HFC composition (mol % and wt %) in IL.
Standard uncertainties: u(T) = 0.1° C.; u(P) = 0.0008 MPa and u($100x_1$) = 0.5 mol %.

TABLE 13

Experimental VLE for HFC-32/[$C_6C_1$im][Cl] and HFC-125/[$C_6C_1$im][Cl] mixtures at 298.15K.

| HFC-32 (1) + [$C_6C_1$im][Cl] (2) | | | HFC-125 (1) + [$C_6C_1$im][Cl] (2) | | |
|---|---|---|---|---|---|
| P (MPa) | $100x_1$ (mol %) | $w_1$ (wt %) | P (MPa) | $100x_1$ (mol %) | $w_1$ (wt %) |
| 0.05 | 2.1 | 0.5 | 0.05 | 4.0 | 2.4 |
| 0.1 | 4.4 | 1.2 | 0.1 | 7.9 | 4.8 |
| 0.2 | 9.2 | 2.5 | 0.2 | 16.0 | 10.2 |

TABLE 13-continued

Experimental VLE for HFC-32/[C$_6$C$_1$im][Cl] and HFC-125/[C$_6$C$_1$im][Cl] mixtures at 298.15K.

| HFC-32 (1) + [C$_6$C$_1$im][Cl] (2) | | | HFC-125 (1) + [C$_6$C$_1$im][Cl] (2) | | |
|---|---|---|---|---|---|
| P (MPa) | 100x$_1$ (mol %) | w$_1$ (wt %) | P (MPa) | 100x$_1$ (mol %) | w$_1$ (wt %) |
| 0.4 | 18.6 | 5.6 | 0.4 | 29.0 | 19.5 |
| 0.6 | 27.2 | 8.8 | 0.6 | 41.4 | 29.6 |
| 0.8 | 34.5 | 11.9 | 0.8 | 54.3 | 41.3 |
| 1.0 | 41.0 | 15.2 | 1.0 | 65.4 | 52.8 |

P—Pressure; 100x$_1$ and w$_1$ - HFC composition (mol % and wt %) in IL.
Standard uncertainties: u(T) = 0.1° C.; u(P) = 0.0008 MPa and u(100x$_1$) = 0.5 mol %.

It is worth mentioning that the absorption equilibrium isotherms shown in FIG. 4 and FIG. 5 were measured up to 1.0 MPa in order to not exceed the saturation vapor pressure at 298.15 K of the HFCs studied here, i.e., 1.69 and 1.38 MPa for HFC-32 and HFC-125, respectively. (Lemmon, E. W. et al., 2013.)

As expected, the solubility of HFC-32 and HFC-125 increased with increasing pressure for any given IL. However, it is the relative differences in solubility for either HFC-32 or HFC-125 that is most important, particularly for selective separation of R-410A. For example, HFC-32 is 44.2% (mole fraction basis) more soluble than HFC-125 in [C$_4$C$_1$im][BF$_4$] at 298.15 K and 1.0 MPa. However, the inventors have realized that the more relevant comparison for designing separation systems is the difference in solubility based on a mass fraction basis. In this case, due to molecular weight differences (HFC-32 MW=52.024 g·mol$^{-1}$ and HFC-125 MW=120.02 g·mol$^{-1}$), HFC-125 is only 11.4% more soluble than HFC-32 at 298.15 K and 1.0 MPa. Similar differences in solubility were found for the other ILs with fluorinated anions, [C$_4$C$_1$im][PF$_6$] and [C$_6$C$_1$im][FAP], as shown in Tables 9 and 10, respectively.

In addition to the anion fluorination of the imidazolium-based ILs, a longer alkyl chain length for the cation played a role in increasing the HFC-32 and HFC-125 absorption in [C$_6$C$_1$im][FAP].

Deviation from Ideality (Raoult's Law)

Figure 6:
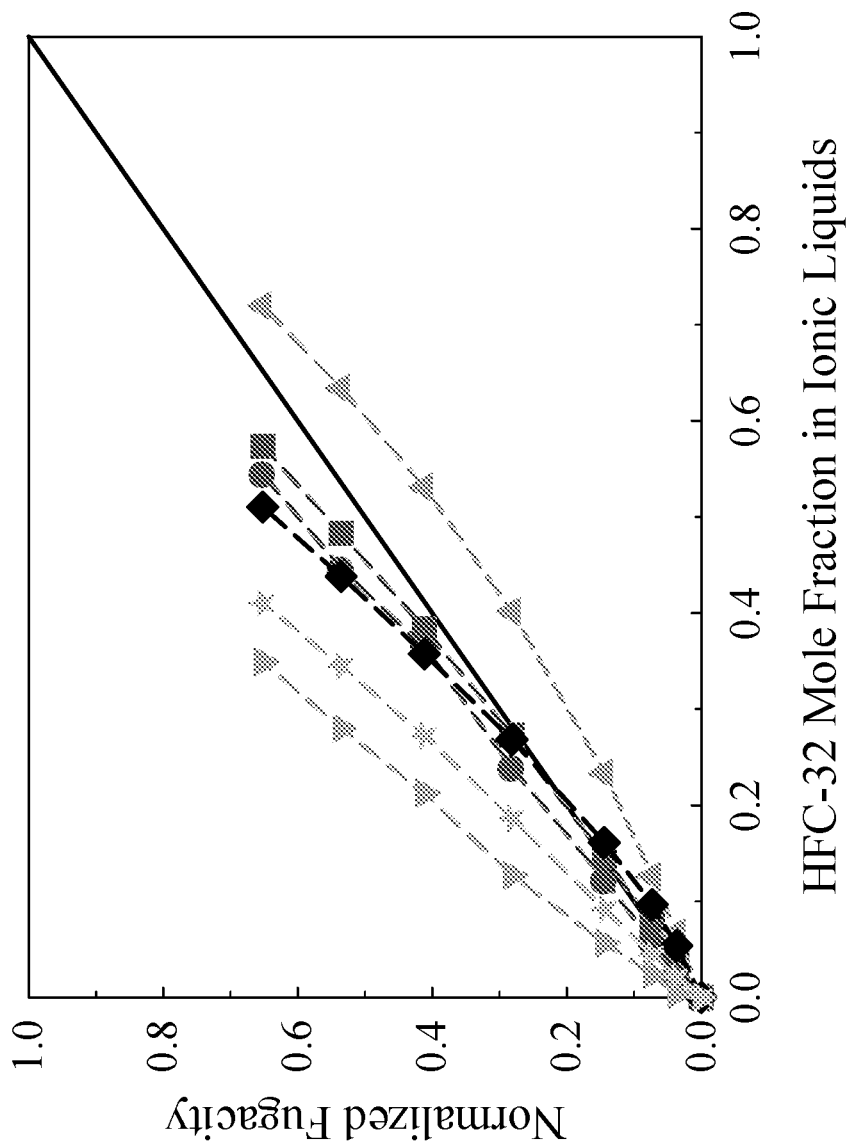
FIG. 6 shows normalized fugacity for HFC-32 in $[C_4C_1im][SCN](\blacktriangledown)$, $[C_6C_1im][Cl](\star)$, $[C_4C_1im][C_1CO_2]$ ($\blacklozenge$), $[C_4C_1im][BF_4](\bullet)$, $[C_4C_1im][PF_6](\blacksquare)$, and $[C_6C_1im][FAP](\blacktriangle)$ as a function of refrigerant molar composition at 298.15 K. Solid line represents Raoult's law. Dashed lines were added as a guide for the reader.
Figure 7:
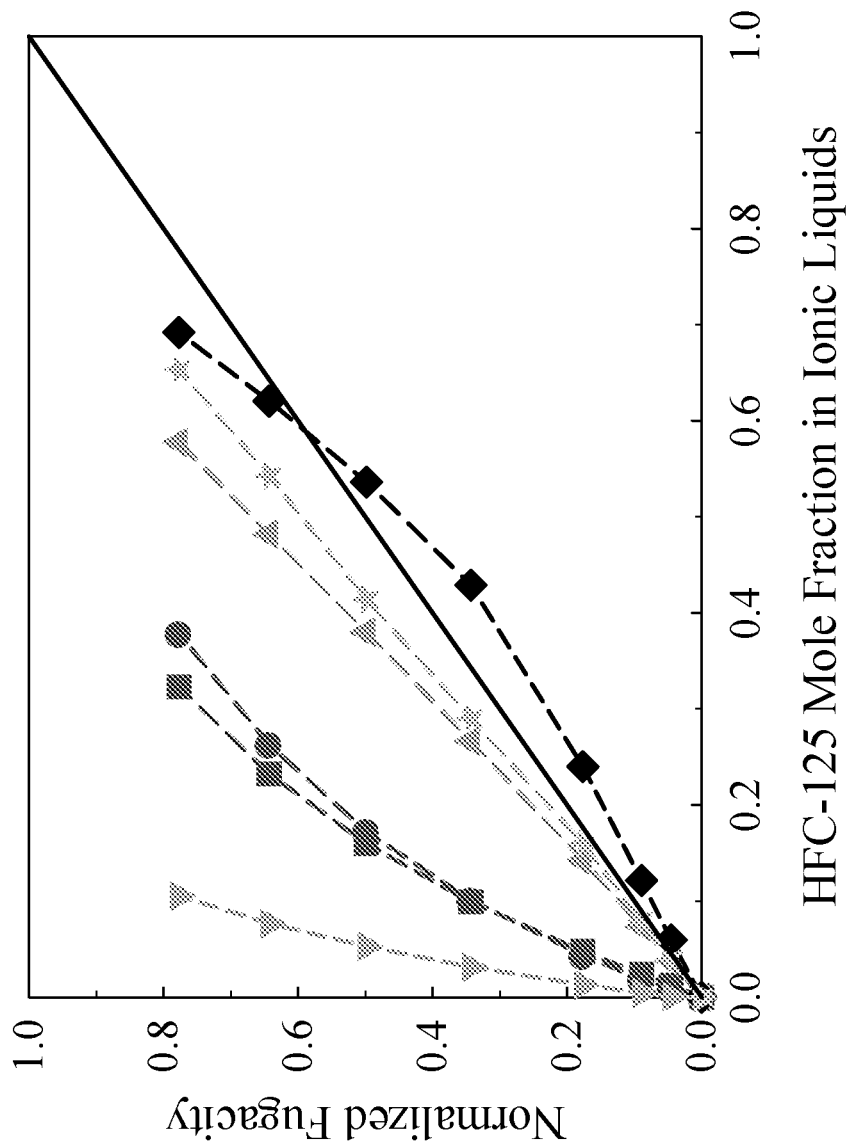
FIG. 7 shows normalized fugacity for HFC-125 in $[C_4C_1im][SCN](\blacktriangledown)$, $[C_4C_1im][PF_6](\blacksquare)$, $[C_4C_1im][BF_4]$ ($\bullet$), $[C_6C_1im][FAP](\blacktriangle)$, $[C_6C_1im][Cl](\star)$, and $[C_4C_1im][C_1CO_2](\blacklozenge)$ as a function of refrigerant molar composition at 298.15 K. Solid line represents Raoult's law. Dashed lines were added as a guide for the reader.

To evaluate the non-ideality of HFC-32 and HFC-125 in IL, the normalized fugacity as a function of HFC molar compositions in the liquid phase was evaluated. The normalized fugacity was expressed as f$^v$/f$^{sat}$, where f$^v$ refers to the vapor phase fugacity of the HFC resulting from the negligible vapor pressure of the IL, such that y$_{ref}$=1, and f$^{sat}$ corresponds to the fugacity of the HFC at saturated vapor pressure with a temperature of 298.15 K. (Street Jr, K. W. et al., Tribol. Trans. 2011, 54, (6), 911-919.) FIG. 6 and FIG. 7 show the normalized fugacity for HFC-32 and HFC-125 in the ILs studied in this example as a function of molar compositions at 298.15 K.

It is most interesting that these refrigerants within the same family of HFCs show quite distinct solubility behaviors depending on the choice of IL. For instance, HFC-32 had a strong negative deviation from Raoult's law in [C$_6$C$_1$im][FAP] across the entire refrigerant composition range, suggesting that the phase behavior was dominated by stronger van der Waals interactions between HFC-32 and this IL. In addition, HFC-32 exhibited a nearly ideal solubility behavior in [C$_4$C$_1$im][C$_1$CO$_2$] and [C$_4$C$_1$im][PF$_6$] for lower refrigerant compositions (up to 0.3 mole fraction), whereas at higher refrigerant mole fractions, it showed a slightly positive deviation from Raoult's law. HFC-32 showed positive deviations over all compositions in [C$_4$C$_1$im][SCN], [C$_4$C$_1$im][BF$_4$] and [C$_6$C$_1$im][Cl]. As noted above, the strong absorption mechanism for HFC-32 in ILs with fluorinated anions is thought to be due to hydrogen bonding between the electronegative fluorinated IL anion (BF$_4$, PF$_6$, and FAP) and the acidic hydrogen atoms on the fluorocarbon (CH$_2$F$_2$). Unlike HFC-32, HFC-125 exhibited a strong positive deviation from Raoult's law in ILs with fluorinated anions (BF$_4$, PF$_6$, and FAP), possibly indicating that the cohesive forces between HFC-125 and the IL are weaker than cohesive forces between HFC/HFC and/or IL/IL. Surprisingly, HFC-125 in [C$_4$C$_1$im][C$_1$CO$_2$] showed mixed negative and positive deviations from Raoult's law depending on the molar concentration of the refrigerant. For instance, HFC-125 exhibited negative deviation for lower refrigerant mole fractions (up to approximately 0.6), whereas, at higher refrigerant compositions, it showed positive deviation from Raoult's law. These results suggest that the carboxylate group in the IL anion plays an important role in increasing the solubility of HFC-125. This is surprising in view of existing wisdom that H-bonding with fluorinated anions is critical for high solubility.

Van Der Waals EoS Modeling

FIG. 4 and FIG. 5 (lines) show the van der Waals EoS model predictions for the solubilities of HFC-32 and HFC-125 in ILs using the best fit parameters reported in Tables 14 and 15, respectively.

TABLE 14 van der Waals EoS model parameters for HFC-32

| | HFC-32/IL van der Waals Parameters | | | | |
|---|---|---|---|---|---|
| Ionic liquid | l$_{ij}$ | l$_{ji}$ | m | τ | β$_{IL}$ |
| [C$_6$C$_1$im][FAP] | 0.76263 | 0.76227 | −3.1790 | 1070.6 | 0.80407 |
| [C$_4$C$_1$im][BF$_4$] | 0.84646 | 0.84015 | −5.2491 | 1492.4 | 0.25646 |
| [C$_4$C$_1$im][PF$_6$] | 0.77015 | 0.76988 | −3.3283 | 1079.2 | 0.96279 |
| [C$_4$C$_1$im][C$_1$CO$_2$] | 0.68425 | 0.68604 | −2.1789 | 1152.3 | 4.9624 |
| [C$_6$C$_1$im][Cl] | 0.86666 | 0.85663 | −5.8300 | 1500.0 | 0.24679 |
| [C$_4$C$_1$im][SCN] | 0.90109 | 0.87156 | −6.72538 | 1499.8 | 0.033817 |

TABLE 15 van der Waals EoS model parameters for HFC-125

| | HFC-125/IL van der Waals Parameters | | | | |
|---|---|---|---|---|---|
| Ionic liquid | l$_{ij}$ | l$_{ji}$ | m | τ | β$_{IL}$ |
| [C$_6$C$_1$im][FAP] | 0.75724 | 0.75777 | −3.1236 | 1096.9 | 0.84396 |
| [C$_4$C$_1$im][BF$_4$] | 0.94755 | 0.88067 | −9.7377 | 1495.6 | −0.19398 |
| [C$_4$C$_1$im][PF$_6$] | 0.63148 | 0.63317 | −1.7454 | 1187.0 | 4.9560 |
| [C$_4$C$_1$im][C$_1$CO$_2$] | 0.40726 | 0.24824 | −0.34565 | 115.93 | 0.053203 |
| [C$_6$C$_1$im][Cl] | 0.79991 | 0.80272 | −4.0687 | 1440.3 | 0.83820 |
| [C$_4$C$_1$im][SCN] | 0.96174 | 0.92967 | −9.9840 | 1.6323 | 0.75431 |

Because ILs decompose before reaching their critical temperatures and actual critical points cannot be determined experimentally, hypothetical values (pseudocritical points) were used for ILs in this analysis. (Rebelo, L. P. et al., J. Phys. Chem. B 2005, 109, (13), 6040-6043; and Rai, N. et al., Faraday discuss. 2012, 154, 53-69.) Multiple studies have sought to predict the pseudocritical points for ILs. For the IL [C$_4$C$_1$im][PF$_6$], pseudocritical property estimation methods include density and surface tension-based empirical equations, group contribution methods, Gibbs ensemble Monte Carlo, and the critical-volume based Vetere's method. (Rebelo, L. P. et al., 2005; Valderrama, J. O. et al., Ind. Eng. Chem. Res. 2009, 48, (14), 6890-6900; Rai, N. et al., 2012; and Yokozeki, A. et al., 2010.) However, these various methods result in estimates for [C$_4$C$_1$im][PF$_6$] pseudocritical temperatures and pressures ranging from 600-1300 K and 0.39-3.0 MPa, respectively. Previous analysis suggested the generic van der Waals model was not sensitive to IL critical properties. (Yokozeki, A. et al., 2010; Yokozeki, A., 2001.) To verify this, a systematic analysis of the model fit was performed, quantified by the sum of residuals squared, with respect to T$_c$ from 600 K to 1400 K and P$_c$ from 0.1 MPa to 5.0 MPa for the mixture of HFC-32 in [C$_4$C$_1$im][PF$_6$] (Data not shown). The results showed that the van der Waals EoS model is insensitive to T$_c$ and P$_c$'s for ILs. Therefore, it is unnecesary to determine highly accurate IL pseudocritical properties when fitting the van der Waals EoS model parameters to binary mixture solubility data. Any critical point estimate can be used if its critical pressure is greater than 0.5 MPa. As mentioned above, the T$_c$ and P$_c$ for each IL were set at 1000 K and 2.5 MPa, respectively.

Figure 8:
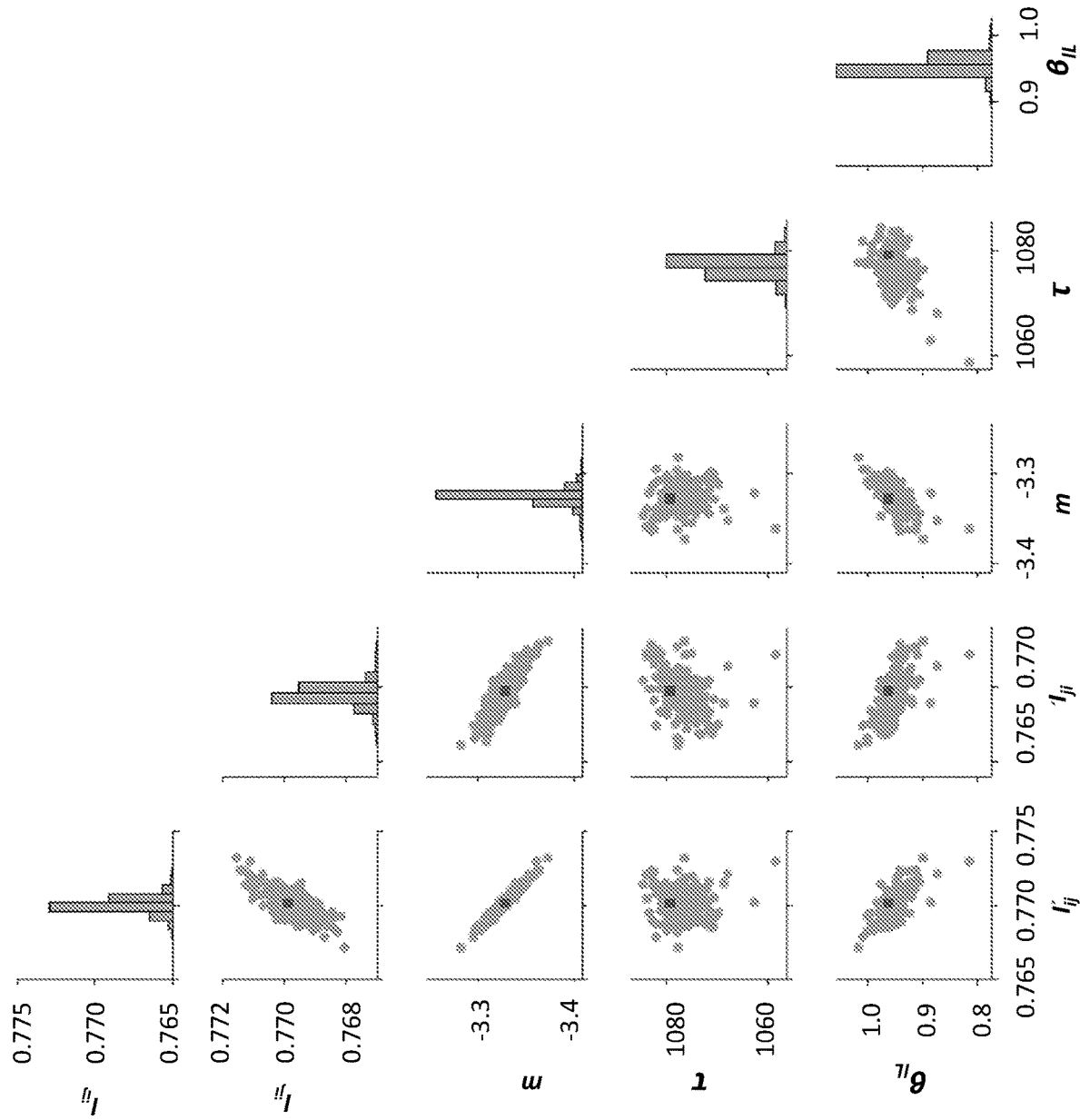
FIG. 8 shows uncertainty analysis of van der Waals equation of state (EoS) model parameters for the solubility of HFC-32 in $[C_4C_1im][PF_6]$. Histograms for each parameter are shown on the diagonal, depicting the variability of each parameter. Scatter plots below the diagonal show the pairwise variability of the fitted parameters, with the dark gray squares indicating the parameters calculated with the original dataset shown in Table 14.

Monte Carlo uncertainty analysis was also performed for the fitted parameters of the mixture of HFC-32 in [C$_4$C$_1$im][PF$_6$]. To summarize, normally distributed random error was added to the experimental x, T, and P in Table 9 to create a new "simulated" experimental dataset. The values of error were chosen to correspond with experimental precision for x, T, and P, and the normal distribution over which the errors were randomly chosen was located within each measurement's standard uncertainty: ±0.005 (unitless) for mole fraction, ±0.1 K for temperature, and +0.0008 MPa for pressure. Using the simulated data, the van der Waals parameters $l_{ij}$, $l_{ji}$, m, τ, and $β_{IL}$ were refit and the results recorded. This procedure was repeated one thousand times. Thus, one thousand simulated experimental datasets, with x, T, and P values varying within the experimental precisions, were generated and van der Waals parameters were fit to each simulated dataset. This provided a multivariate distribution of the fitted parameters, which is shown in FIG. 8. The Monte Carlo procedure provides the expected deviation in the fitted results if the experiments were repeated hundreds of times.

Three important insights about the experimental data and fitted model can be gained from FIG. 8. The plots along the diagonal of FIG. 8 are histograms for the five fitted parameters. The first insight is that parameter $l_{ij}$ has a variability of 0.785%, $l_{ji}$ has a variability of 0.454%, m has a variability of 2.66%, τ has a variability of 2.44%, and $l_{ij}$ has a variability of 25.0%. This variability is induced by random errors of similar magnitude to the experimental precision. In other words, a variability of at least this large is expected if the experiments were repeated with the same equipment. The variability of fitted parameter $β_{IL}$ is one to two orders of magnitude larger than the other parameters. This gives the second insight: $β_{IL}$ is a sloppy parameter, which means it cannot be determined uniquely from these data. (Chis, O.-T. et al., Math. biosc. 2016, 282, 147-161.) This is because the quality of fit (sum of residuals squared) is insensitive with respect to $β_{IL}$. Scatter plots below the diagonal of FIG. 8 show pairwise variability in the fitted parameters. The highest histogram bars (on the diagonal) correspond with the tightest clusters of parameters in the scatter plots (off the diagonal). The dark gray squares mark the parameter values for HFC-32 in [C$_4$C$_1$im][PF$_6$] reported in Table 14, which were calculated with the original experimental data from Table 9. In each scatter plot, this dark gray square is located in the densest regions of parameters. A third key insight comes from these scatter plots: parameters $l_{ij}$, $l_{ji}$, m, and $β_{IL}$ are correlated. This suggests there exists an alternate thermodynamic model with one or fewer fitted parameters that gives a similar quality of fit (sum of residuals squared).

Ideal Selectivity Based on Henry's Law Constants

The most suitable IL for a specific gas separation process hinges on the gas absorption capacity, the ability to preferentially absorb one gas over another from a mixture, and the ability to facilitate gas diffusion (as discussed above). In this context, the ideal selectivity is a parameter that may be used to assess the ability of a given pure IL to separate HFC-32 and HFC-125 in R-410A. The ideal selectivity can be defined as the ratio of the Henry's law constants of the HFC refrigerants at a given temperature, as follows: (Sosa, J. E. et al., Ind. Eng. Chem. Res. 2019, 58, (45), 20769-20778.)

$$S_{Hij} = \left(\frac{k_{Hi}}{k_{Hj}}\right)_T \quad (22)$$

where $k_{Hi}$ and $k_{Hj}$ are the Henry's law constants calculated for the HFC refrigerants, i=HFC-32 and j=HFC-125, respectively.

Henry's law constants for HFC-32 and HFC-125 in the ILs were calculated using the method described above, and the results are summarized in Table 16.

TABLE 10

Henry's law constants (MPa) for HFC-32 and HFC-125 in ILs at 298.15K.[a]

| Ionic liquid | Henry's law constants ($k_H$) (kH, MPa) | | Selectivity |
| --- | --- | --- | --- |
| | HFC-32 | HFC-125 | $S_{Hij}$ |
| [C$_4$C$_1$im][BF$_4$] | 1.54 ± 0.06 | 4.19 ± 0.17 | 0.37 |
| [C$_4$C$_1$im][PF$_6$] | 1.34 ± 0.01 | 4.05 ± 0.06 | 0.33 |
| [C$_6$C$_1$im][FAP] | 0.84 ± 0.03 | 1.37 ± 0.01 | 0.61 |
| [C$_4$C$_1$im][C$_1$CO$_2$] | 1.20 ± 0.11 | 0.81 ± 0.00 | 1.48 |
| [C$_4$C$_1$im][SCN] | 3.11 ± 0.37 | 13.32 ± 2.44 | 0.23 |
| [C$_6$C$_1$im][Cl] | 2.00 ± 0.00 | 1.16 ± 0.03 | 1.72 |

[a]The uncertainties are the standard error of the coefficient obtained in the linear regression.

Comparing the Henry's law constants calculated for HFC-32 in ILs at 298.15 K shows that $k_H$ (MPa) follows the order: [C$_6$C$_1$im][FAP]<[C$_4$C$_1$im][C$_1$CO$_2$]<[C$_4$C$_1$im][PF$_6$]<[C$_4$C$_1$im][BF$_4$]<[C$_6$C$_1$im][Cl]<[C$_4$C$_1$im][SCN]. However, HFC-125 $k_H$ (MPa) follows the order: [C$_4$C$_1$im][C$_1$CO$_2$]<[C$_6$C$_1$im][Cl]<[C$_6$C$_1$im][FAP]<[C$_4$C$_1$im][PF$_6$]<[C$_4$C$_1$im][BF$_4$]. Based on this analysis, the ILs with the highest solubility (i.e. lowest Henry's law constants) for HFC-32 and HFC-125 are [C$_6$C$_1$im][FAP] and [C$_4$C$_1$im][C$_1$CO$_2$], respectively.

The ideal selectivity can also be defined as the ratio of the pure refrigerant solubilities on a molar or mass basis in the IL. As discussed above, the mass basis is more relevant to the design of separation systems; therefore, the selectivity can be defined as follows:

$$S_{Wij} = \left(\frac{w_{vi}/w_{li}}{w_{vj}/w_{lj}}\right)_{T,P} \quad (23)$$

where $w_{vi,j}$ and $w_{li,j}$ are the vapor and liquid mass fractions of the dissolved refrigerants (i=HFC-32 and j=HFC-125) in the IL at T=298.15 K and P=1.0 MPa, respectively (where $w_{vi}$ and $w_{vj}$=1.0).

Figure 9:
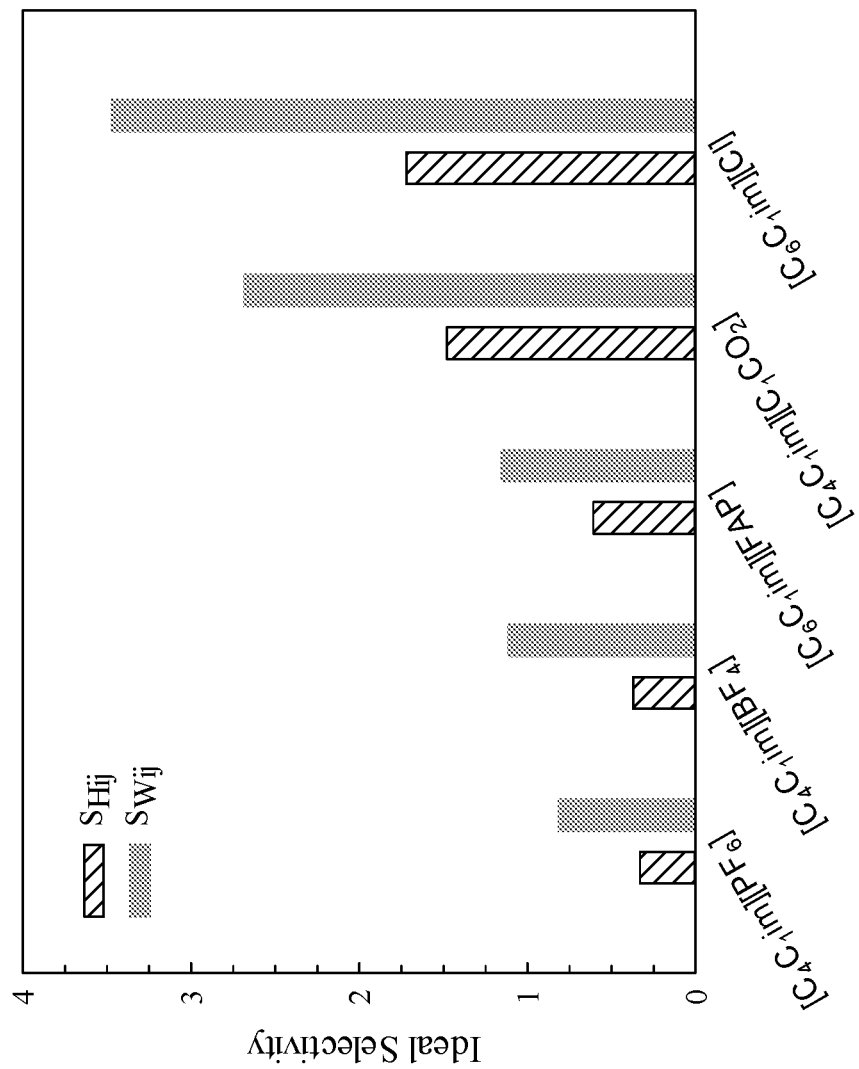
FIG. 9 shows ideal selectivity for the absorption of HFC-32 and HFC-125 in ILs. The ideal selectivity was calculated based on the ratio of the Henry's law constants $(S_{Hij})$ in the ILs at 298.15 K and the ratio of the weight fractions $(S_{Wij})$ in the ILs at 1.0 MPa and 298.15 K.
Figure 10B:
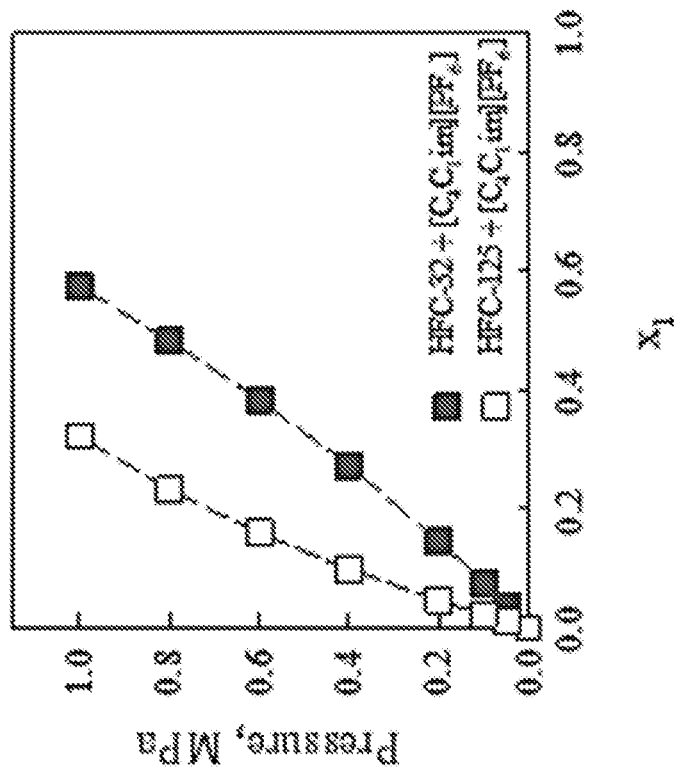
FIGS. 10A-10F show comparison of HFC-32 and HFC-125 VLE (mol fraction, $x_j$) in ionic liquids.
Figure 10A:
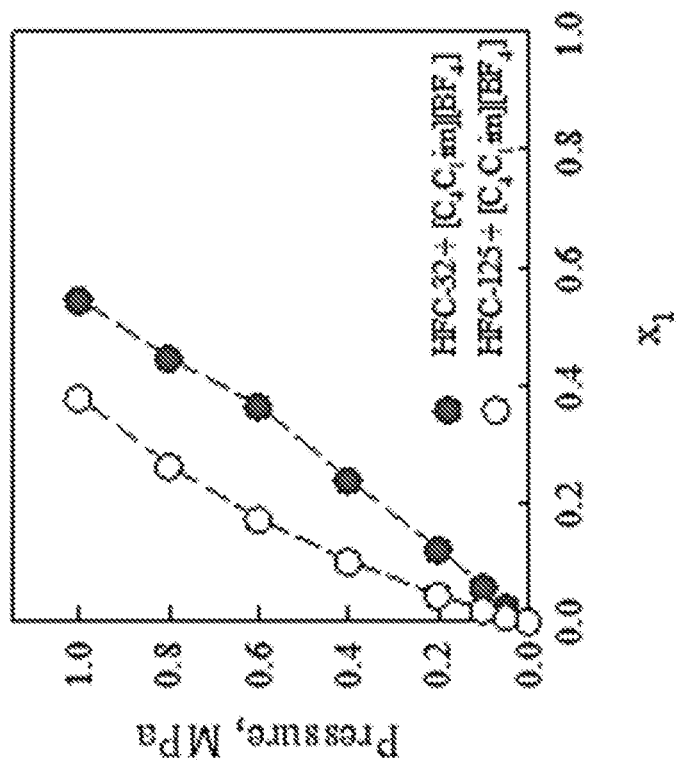
Figure 10D:
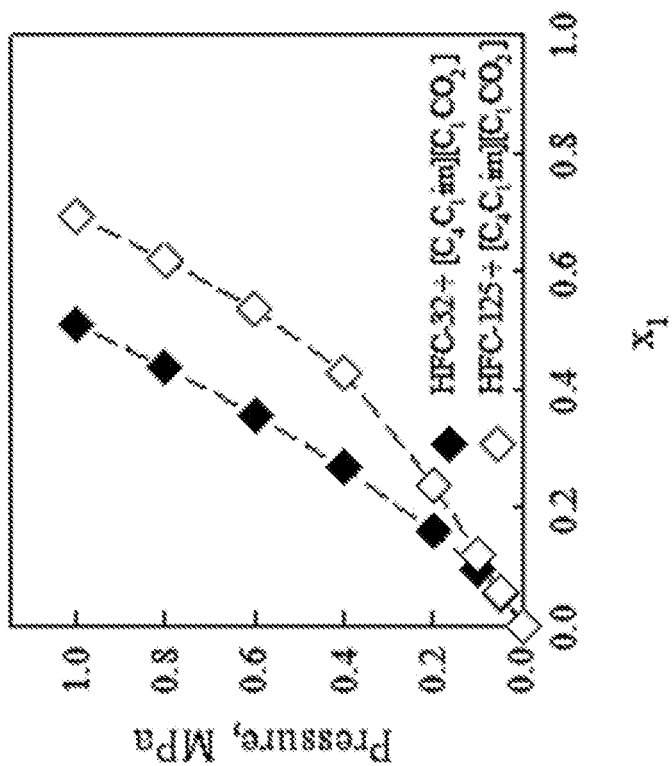
Figure 10C:
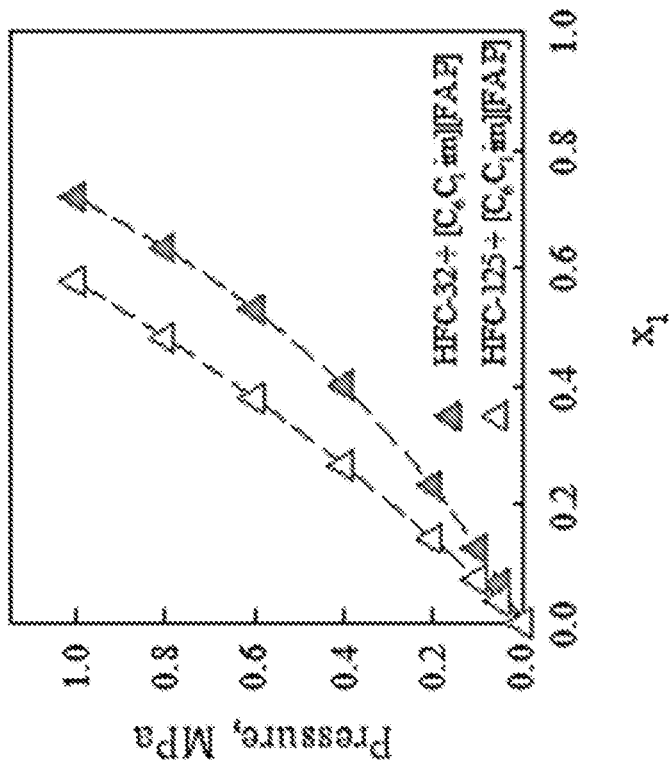
Figure 10F:
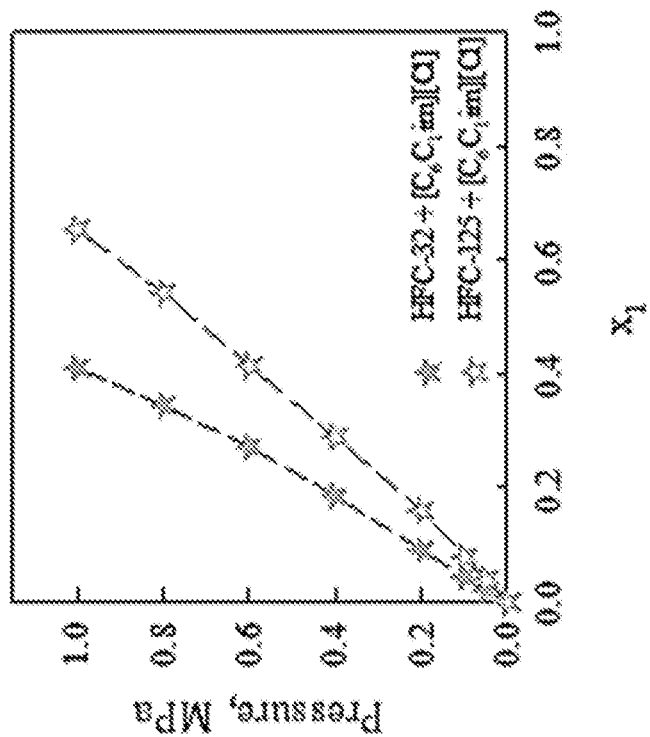
Figure 10E:
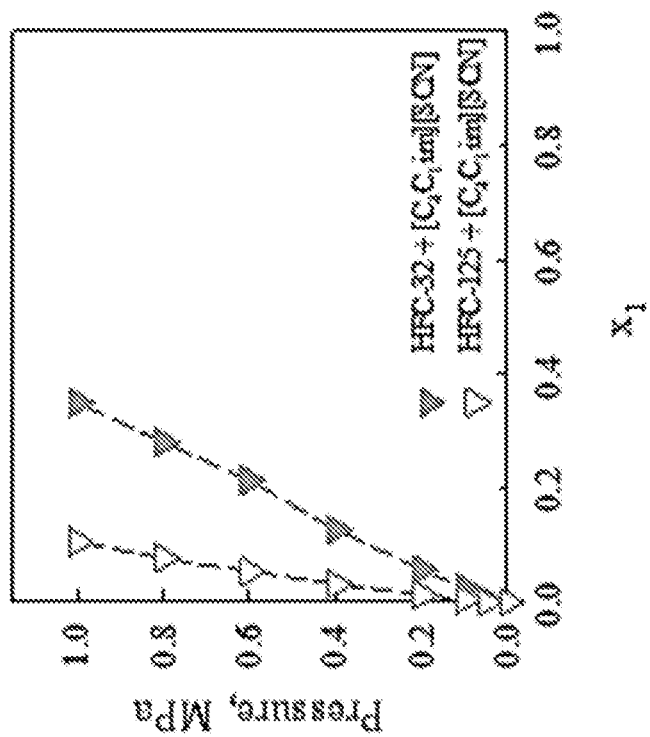
Figure 11D:
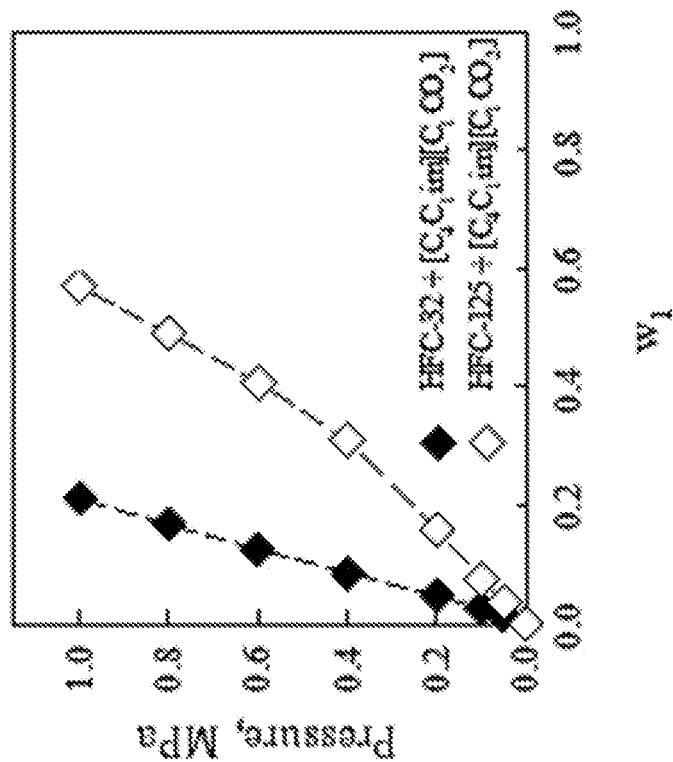
Figure 11C:
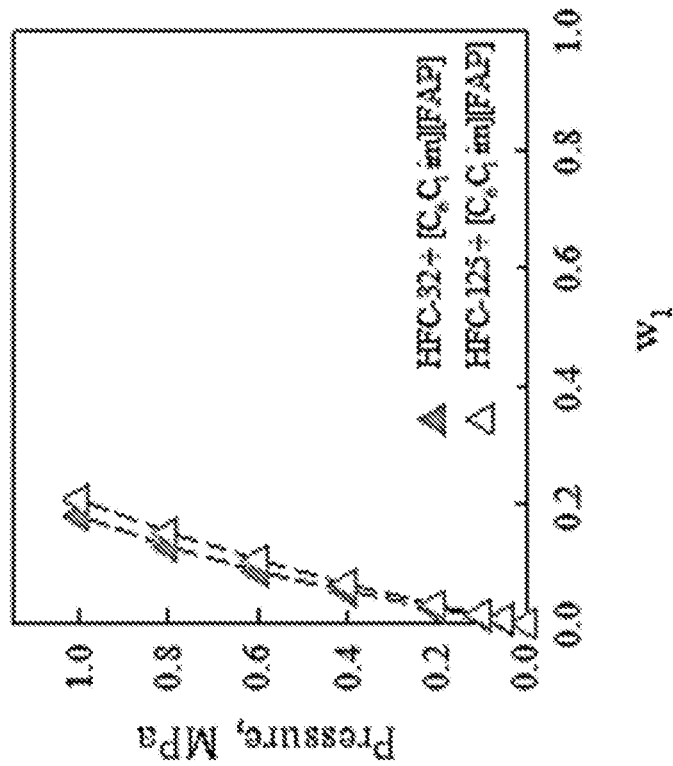
Figure 11F:
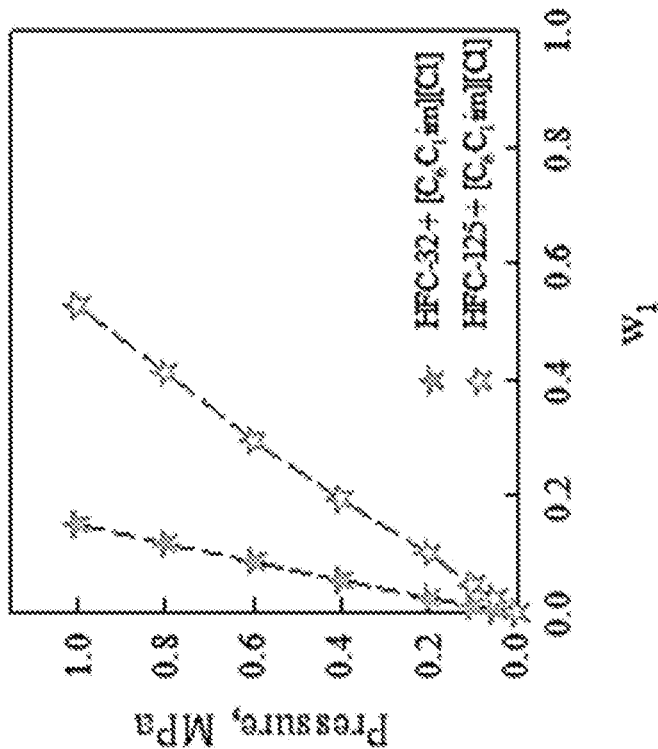
Figure 11E:
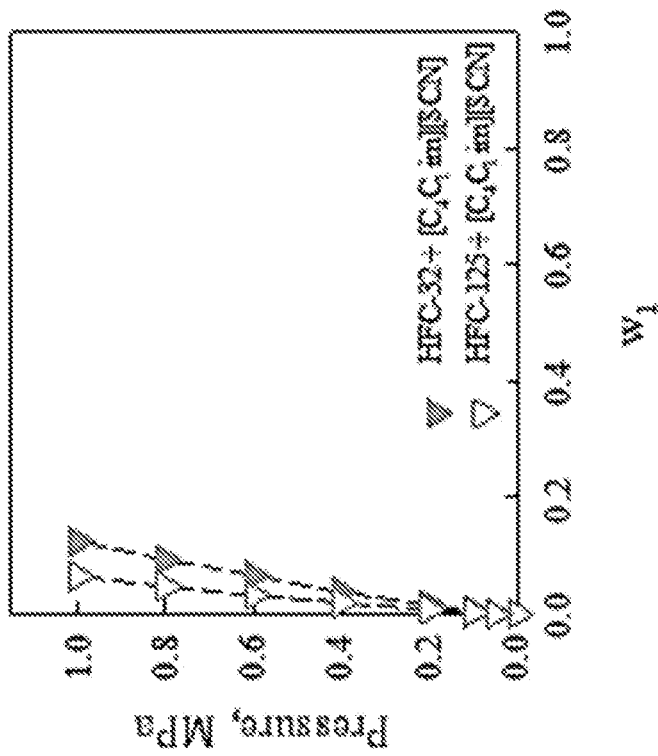

In both cases ($S_{Hij}$ and $S_{Wij}$), the IL with the highest overall selectivity for the separation of R-410A, based on the ratio of the Henry's law constants ($S_{Hij}$) or the ratio of the mass fractions ($S_{Wij}$) was [C$_6$C$_1$im][Cl] The ideal selectivity trends obtained with Equations 22 and 23 are shown in FIG. 9.

It is emphasized again that existing wisdom has been to compare the mole fraction solubility as a function of T and P in selecting an IL for the most efficient separation (FIGS. 10A-10F). However, the most relevant comparison for designing a separation process is to evaluate the difference in the mass fraction solubility as a function of T and P (FIGS. 11A-11F).

In some cases such as for [C$_4$C$_1$im][BF$_4$], [C$_4$C$_1$im][PF$_6$], and [C$_6$C$_1$im][FAP] what appears to be a large difference in the mole fraction solubility for HFC-32 and HFC-125 turns out to be only a small or negligible difference in the mass fraction solubility. Thus, selecting these ILs would not result in an efficient separation. By contrast, small differences in the mole fraction solubility for HFC-32 and HFC-125 in [C$_4$C$_1$im][C$_1$CO$_2$] and [C$_6$C$_1$im][Cl] result in larger differences in mass fraction solubility, and therefore these two ILs are actually superior candidates for the separation of R-410A.

Fickian Diffusion Coefficients

The diffusivity of HFCs in ILs also affects the time-dependent absorption behavior of HFC-32 and HFC-125 in the ILs was analyzed using a simplified Fickian diffusion model (see above). The calculated diffusion coefficients for HFC-32 and HFC-125 in each IL at 0.05 MPa and 298.15 K are shown in Table 17 along with the viscosity of the ILs at 298.15 K.

romethane, CHClF$_2$) in [C$_4$C$_1$im][BF$_4$] and [C$_4$C$_1$im][PF$_6$] are also within the same order of magnitude ($10^{-10}$ to $10^{-11}$ m$^2$·s$^{-1}$) as the data reported here. (Minnick, D. L. et al., *Ind. Eng. Chem. Res.* 2019, 58, (25), 11072-11081.) The trend in diffusion coefficient with the inverse in viscosity (D~1/μ) generally holds true for HFC-32 and HFC-125, except for HFC-32+[C$_4$C$_1$im][C$_1$CO$_2$], which might indicate some chemical interaction between HFC-32 and the acetate anion [C$_1$CO$_2$]. Molecular modeling studies are underway to elucidate this effect.

Conclusions

A separation process for recycling R-410A is important so that HFC-32 can be reused in new HFC containing low-GWP refrigerant blends, and HFC-125 can be used as a fluorine-containing feedstock. The absorption of HFC-32 and HFC-125 in six imidazolium-based ILs containing fluorinated and non-fluorinated anions was accurately measured using a microbalance at 298.15 K and pressures ranging from 0.05 to 1.0 MPa. HFC-32 was found to be more soluble in ILs with fluorinated anions than HFC-125, which is most likely due to hydrogen bonding between the refrigerant (CH$_2$F$_2$) and the fluorinated anion ([BF$_4$], [PF$_6$], and [FAP]). However, HFC-125 was found to be more soluble in ILs with non-fluorinated anions ([C$_1$CO$_2$] and [Cl]). The [C$_4$C$_1$im][SCN] had low solubility for both HFC-32 and HFC-125 relative to the other ILs tested. The experimental VLE data sets were successfully correlated using the van der Waals EoS, and the model was insensitive to the choice of critical parameters (600<$T_c$<1400 K and 0.5<$P_c$<5.0 MPa). The [C$_6$C$_1$im][Cl] and [C$_4$C$_1$im][C$_1$CO$_2$] ILs provided the highest ideal selectivity (2.7 to 3.5 on a mass basis) for separating R-410A at 298.15 K among the ILs studied in this

TABLE 17

Estimated Fickian diffusion coefficients for HFC-32/IL and HFC-125/IL systems at 298.15K and 0.05 MPa and reported viscosities for ILs at 298.15K and 0.1 MPa.[a]

| Ionic liquid | Viscosity (Pa · s) | HFC-32 (1)/IL (2) | | HFC-125 (1)/IL (2) | |
|---|---|---|---|---|---|
| | | D ($10^{-11}$ m$^2$·s$^{-1}$) | $C_s$ (wt %) | D ($10^{-11}$ m$^2$·s$^{-1}$) | $C_s$ (wt %) |
| [C$_6$C$_1$im][Cl] | 18.1 ± 1.8 | 1.5 | 0.5 | 0.4 | 3.2 |
| [C$_4$C$_1$im][C$_1$CO$_2$] | 0.448 ± 0.019 | 0.5 | 1.5 | 1.3 | 3.7 |
| [C$_4$C$_1$im][PF$_6$] | 0.271 ± 0.021 | 8.5 | 0.7 | 1.7 | 0.5 |
| [C$_4$C$_1$im][BF$_4$] | 0.1014 ± 0.0027 | 7.8 | 0.6 | 2.4 | 0.4 |
| [C$_6$C$_1$im][FAP] | 0.0882 ± 0.0021 | 19.6 | 0.6 | 5.5 | 0.8 |
| [C$_4$C$_1$im][SCN] | 0.0517 ± 0.00055 | — | — | — | — |

[a]The estimated diffusivity uncertainty was estimated to be within a factor of two in the calculated diffusivity.[13]

The diffusion coefficient (D) of HFCs in the ILs is dependent on the refrigerant solubility ($C_s$), the viscosity of the IL, and the molecular radius of the solute molecule, according to the Stokes-Einstein equation. (Yokozeki, A., 2002; and Reid, R. C. et al., *The Properties of Gases and Liquids.* McGraw Hill: New York, USA, 1987.) The largest D values for HFC-32 and HFC-125 were found in [C$_6$C$_1$im][FAP] (HFC-32 D=19.6×10$^{-11}$ m$^2$·s$^{-1}$ and HFC-125 D=5.5× 10$^{-11}$ m$^2$·s$^{-1}$), which has one of the lowest viscosities of the ILs tested. The 3.5 times higher HFC-32 diffusion coefficient in [C$_6$C$_1$im][FAP] can be attributed to the approximately 22% smaller molecular radius for HFC-32 (0.18 nm) relative to HFC-125 (0.23 nm). (Yokozeki, A. et al., *Inter. J. Thermophys.* 1998, 19, (1), 89-127; and Morais, A. R. et al., *AIChEJ.* 2020.) The diffusion coefficients for HFC-32 and HFC-125 in ILs are on the same order of magnitude, i.e. between 10$^{-11}$ and 10$^{-10}$ m$^2$·s$^{-1}$, for those previously reported in other fluorinated ILs. (Shiflett et al., 2006.) In addition, the diffusion coefficient for R-22 (chlorodifluoexample. The one-dimensional diffusion model was applied to time-dependent absorption data for each HFC/IL binary system. HFC-32 and HFC-125 had a higher diffusion coefficient in [C$_6$C$_1$im][FAP] relative to the other ILs due to its lower viscosity. HFC-32 had a higher diffusion coefficient (up to 3.5 for [C$_6$C$_1$im][FAP]) relative to HFC-125 due to its smaller molecular radius (0.18 nm versus 0.25 nm. The present example provides important insights into the solubility, diffusivity, EoS modeling, and ideal selectivity of HFC-32 and HFC-125 in ILs for the design of a separation process for recycling R-410A.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more."

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A process for separating an azeotropic mixture, the process comprising exposing an azeotropic mixture comprising a first (hydro) fluorocarbon and a second (hydro) fluorocarbon to an ionic liquid comprising a cation and a non-fluorinated anion at a temperature and a pressure at which the ionic liquid absorbs more of one of the first and second (hydro) fluorocarbons than another of the first and second (hydro) fluorocarbons to form a (hydro) fluorocarbon-containing ionic liquid and a processed azeotropic mixture, wherein the ionic liquid is a non-fluorinated ionic liquid and the cation is a non-fluorinated cation, further wherein the azeotropic mixture comprises difluoromethane as the first (hydro) fluorocarbon and pentafluoroethane as the second (hydro) fluorocarbon, further wherein the ionic liquid is selected from imidazolium chloride, imidazolium acetate, and combinations thereof, and the imidazolium is 1-butyl-3-methylimidazolium or 1-hexyl-3-methylimidazolium, and further wherein the ionic liquid is selected based on a relative difference in solubilities of the first and second (hydro) fluorocarbons in the ionic liquid as determined on a mass fraction basis.

* * * * *

UNITED STATES PATENT AND TRADEMARK OFFICE
CERTIFICATE OF CORRECTION

| | | |
|---|---|---|
| PATENT NO. | : 12,404,224 B2 | Page 1 of 1 |
| APPLICATION NO. | : 17/768287 | |
| DATED | : September 2, 2025 | |
| INVENTOR(S) | : Mark Brandon Shiflett et al. | |

It is certified that error appears in the above-identified patent and that said Letters Patent is hereby corrected as shown below:

In the Specification

Column 7, Line 24:
Delete the phrase "$R^7, R^1, R^9$, and $R^{10}$" and replace with --$R^7, R^8, R^9$, and $R^{10}$--.

Column 7, Line 60:
Delete the phrase "$R^1, R^9$, and $R^{10}$" and replace with --$R^8, R^9$, and $R^{10}$--.

Signed and Sealed this
Thirtieth Day of September, 2025

John A. Squires
*Director of the United States Patent and Trademark Office*